(12) United States Patent
Begg et al.

(10) Patent No.: US 8,907,594 B2
(45) Date of Patent: Dec. 9, 2014

(54) COOLING SYSTEMS AND METHODS

(75) Inventors: Michael Colin Begg, West Sussex (GB); Frederick Thomas Goldie, West Sussex (GB)

(73) Assignee: Tesla Engineering Ltd., West Sussex (GB)

( * ) Notice: Subject to any disclaimer, the term of this patent is extended or adjusted under 35 U.S.C. 154(b) by 287 days.

(21) Appl. No.: 13/148,000

(22) PCT Filed: Feb. 9, 2010

(86) PCT No.: PCT/WO2010/000231
§ 371 (c)(1),
(2), (4) Date: Aug. 4, 2011

(87) PCT Pub. No.: WO2010/089574
PCT Pub. Date: Aug. 12, 2010

(65) Prior Publication Data
US 2011/0285327 A1    Nov. 24, 2011

(51) Int. Cl.
| H05H 7/00 | (2006.01) |
| H05H 11/00 | (2006.01) |
| H05H 13/00 | (2006.01) |
| H05H 13/02 | (2006.01) |
| H01F 6/04 | (2006.01) |

(52) U.S. Cl.
CPC ............... *H05H 11/00* (2013.01); *H05H 7/00* (2013.01); *H05H 13/00* (2013.01); *H01F 6/04* (2013.01); *H05H 13/02* (2013.01)
USPC .......................................... 315/502; 505/163

(58) Field of Classification Search
CPC ............ H05H 13/00; H01F 6/04; F25D 19/00
USPC .......................................... 315/502; 505/163
See application file for complete search history.

(56) References Cited

U.S. PATENT DOCUMENTS 4,507,616 A * 3/1985 Blosser et al. ................ 315/502
4,633,125 A * 12/1986 Blosser et al. .................. 313/62

(Continued)

FOREIGN PATENT DOCUMENTS

| CN | 1794004 | 6/2006 |
| CN | 101361156 | 2/2009 |

(Continued)

OTHER PUBLICATIONS

Chinese Office Action dated Dec. 24, 2012, Chinese Patent Application No. 200880102830.8.

(Continued)

*Primary Examiner* — Alexander H Taningco
*Assistant Examiner* — David Lotter
(74) *Attorney, Agent, or Firm* — Vierra Magen Marcus LLP

(57) ABSTRACT

An ion therapy system comprises a particle accelerator (1) mounted on a rotatable gantry (2). The particle accelerator includes a superconducting coil (17) which rotates about its axis as the particle accelerator rotates about the gantry axis in use to direct an output beam towards a target from different directions. The particle accelerator is rotatable through (180) degrees to move the beam through a corresponding arc. The particle accelerator includes cooling system arranged to cool the coil as the coil rotates. The superconducting coil (17) is mounted in a coil support (25). The coil is surrounded by a cryogen chamber (32) which is located radially outwardly from the coil (17) on the other side of the support (25). The cryogen chamber is in fluid communication with a cryogen recondensing unit (29) whereby vaporized cryogen may flow from the cryogen chamber (32) to the cryogen recondensing unit (29) to be recondensed in use before returning to the cryogen chamber. Thermally conductive means (40) is arranged to facilitate heat transfer from the superconducting coil (17) to the cryogen chamber (32) to vaporize cryogen contained therein in use and thereby remove heat from the coil.

25 Claims, 13 Drawing Sheets

(56) References Cited

U.S. PATENT DOCUMENTS

| | | | | |
|---|---|---|---|---|
| 4,803,433 | A | | 2/1989 | McBride |
| 6,107,905 | A | * | 8/2000 | Itoh et al. ............... 335/216 |
| 2004/0056541 | A1 | | 3/2004 | Steinmeyer |
| 2006/0218942 | A1 | | 10/2006 | Atkins |
| 2006/0236709 | A1 | * | 10/2006 | Steinmeyer ............. 62/259.2 |
| 2008/0093567 | A1 | * | 4/2008 | Gall ........................ 250/493.1 |
| 2009/0038318 | A1 | * | 2/2009 | Begg et al. ................. 62/47.1 |

FOREIGN PATENT DOCUMENTS

| | | | |
|---|---|---|---|
| DE | 102006035094 | B3 | 4/2008 |
| EP | 1437821 | A2 | 7/2004 |
| EP | 1522867 | A2 | 4/2005 |
| EP | 1670128 | A2 | 6/2006 |
| FR | 2560421 | A1 | 8/1985 |
| GB | 2335973 | A | 10/1999 |
| GB | 2432259 | A | 5/2007 |
| GB | 2451708 | A | 11/2009 |
| WO | 2007061937 | A2 | 5/2007 |

OTHER PUBLICATIONS

Office Action dated Mar. 25, 2011, European Patent Application No. EP08776071.6.
Search Report dated Jul. 25, 2008, GB Patent Application No. GB0722098.1.
Examination Report dated Jul. 28, 2010, GB Patent Application No. GB0722098.1.
Examination Report dated Jan. 12, 2011, GB Patent Application No. GB0722098.1.
Examination Report dated May 9, 2011, GB Patent Application No. GB0722098.1.
PCT Search Report dated Sep. 23, 2008, PCT Patent Application No. PCT/GB08/002564.
Office Action dated Jun. 8, 2011, U.S. Appl. No. 11/937,573.
Combined Search and Examination Report dated May 28, 2009, GB Patent Application No. GB0902140.3.
Examination Report dated Apr. 13, 2011, GB Patent Application No. GB0902140.3.
Notification of Grant dated Jul. 26, 2011, GB Patent Application No. GB0902140.3.
PCT International Search Report dated Jul. 16, 2010, PCT Patent Application No. PCT/GB10/000231.
PCT Written Opinion of the International Searching Authority dated Jul. 16, 2010, PCT Patent Application No. PCT/GB10/000231.
Response to UK Search and Examination Report dated Feb. 23, 2011, UK Patent Application No. UK0902140.3.
Response to UK Examination Report dated Jun. 13, 2011, UK Patent Application No. UK0902140.3.
Chinese Office Action dated Sep. 8, 2011, Chinese Patent Application No. 200880102830.8.
Amendment to the Claims, dated Apr. 22, 2010, United Kingdom Patent Application No. GB0722098.1.
Response to Official Letter, dated Nov. 29, 2010, United Kingdom Patent Application No. GB0722098.1.
Response to Official Letter, dated Mar. 14, 2011, United Kingdom Patent Application No. GB0722098.1.
Response to Official Letter, dated May 6, 2011, United Kingdom Patent Application No. GB0722098.1.
Examiner Intention to enter application into grant process dated May 12, 2011, United Kingdom Patent Application No. GB0722098.1.
Claims to be granted, United Kingdom Patent Application No. GB0722098.1.
Written Opinion of the International Searching Authority dated Sep. 30, 2008, PCT Appl. PCT1GB2008/002564, filed Jul. 25, 2008.
English Translation of Description and Claims of DE102006035094.
English Translation of Description and Claims of FR2560421.
E.D. Marquardt, J.P. Le, and Ray Radebaugh, "Cryogenic Material Properties Database," 11th international cryocooler conference, 2000.
Preliminary Amendment dated Mar. 9, 2009, U.S. Appl. No. 11/937,573.
Response to Office Action dated Aug. 31, 2011, U.S. Appl. No. 11/937,573.
Office Action dated Nov. 22, 2011, U.S. Appl. No. 11/937,573.
Green, Cryocoolers and Cryogenic Technique for 4.2 K Devices, Cryopackaging Workshop, ISEC, Manly, Australia, Jul. 8, 2003.
Taylor, et al., "An efficient cooling loop for connecting cryocooler to a helium reservoir," Anchorage, Alaska, Sep. 2003.
Jastec Cryocoolers, www.jastec.org/eg/product/mureibai/mureibai.htm, Aug. 2007.
Chandratilleke, et al., "Development of multi-loop heat pipes for superconducting magnet applications," Advances in Cryogenic Engineering 998, vol. 43 (B), pp. 1513-1519, New York, Aug. 1998.
2nd Chinese Office Action dated Jun. 4, 2012, Chinese Patent Application No. 200880102830.8.
4th Chinese Office Action dated Sep. 17, 2013, Chinese Patent Application No. 200880102830.8.
1st Chinese Office Action dated Sep. 29, 2013, Chinese Patent Application No. 201080007085.6.
English Abstract of CN101361156 published Feb. 4, 2009.
Interview Summary mailed Mar. 19, 2012 in U.S. Appl. No. 11/937,573 filed Nov. 9, 2007.
Notice of Abandonment mailed Jun. 11, 2012 in U.S. Appl. No. 11/937,573 filed Nov. 9, 2007.
Response to 2nd Chinese Office Action dated Aug. 10, 2012, Chinese Patent Application No. 200880102830.8.
English Translation of Amended Claims submitted with Response to 2nd Chinese Office Action dated Aug. 10, 2012, Chinese Patent Application No. 200880102830.8.

* cited by examiner

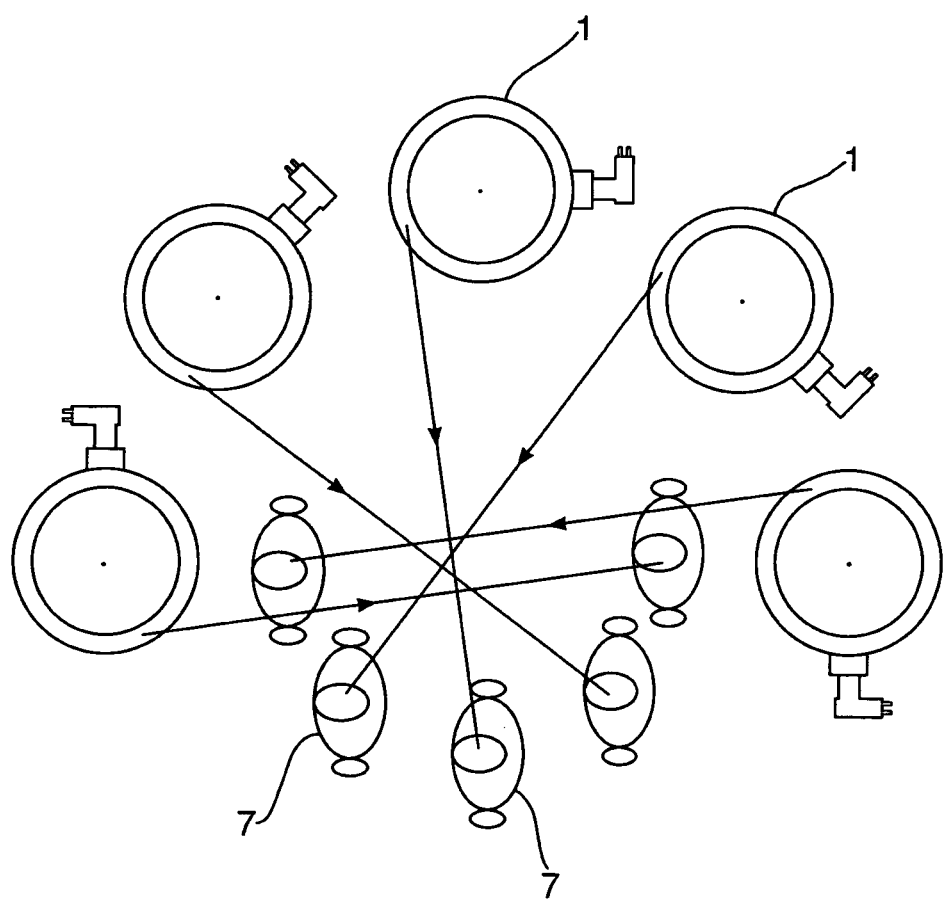

Fig.6.
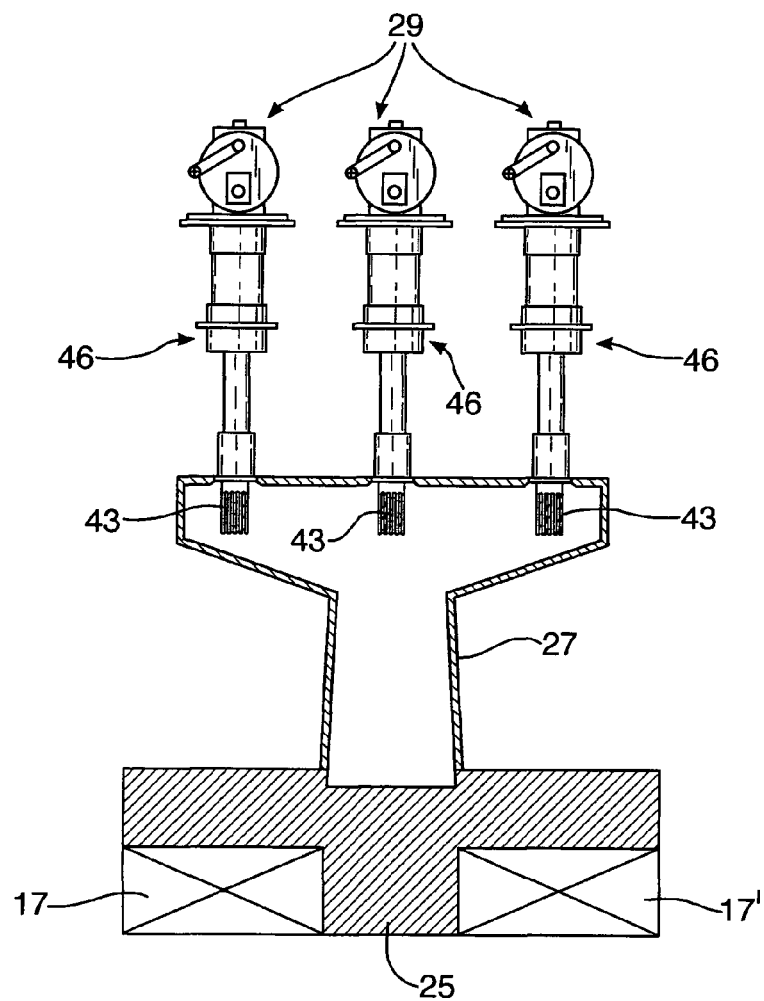
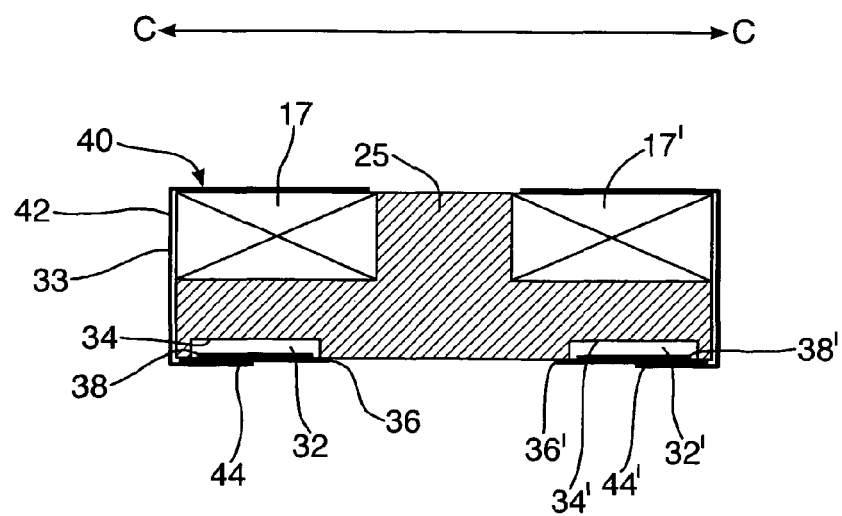

COOLING SYSTEMS AND METHODS

The present application is a Section 371 National Stage Application of International Application No. PCT/GB2010/000231, filed on Feb. 9, 2010, which claims the benefit of GB0902140.3, filed on Feb. 9, 2009, the entire disclosures of both application are incorporated herein by reference in their entirety.

The present invention relates to cooling systems and methods for particle accelerators including one or more superconducting coils, and more particularly to cooling systems and methods for rotatable particle accelerators including one or more superconducting coils.

Particle accelerators are used in many applications, including, for example, particle physics applications, and ion therapy e.g. heavy ion or proton therapy. In certain applications, it is desirable to be able to direct the output beam so as to be incident upon a target from a number of different directions. Such techniques are often used in ion therapy applications to try to irradiate a target structure, such as a tumour, while reducing the radiation dose to surrounding healthy tissues.

In some conventional systems, directing of the output beam may be achieved using a static particle accelerator to supply a particle beam, and providing a steering system to direct the particle beam upon a target from a number of directions. Such systems are typically relatively large and expensive, often requiring a complex system of steering and focussing magnets to direct a beam from the particle accelerator to the target, which may be located at some distance from the accelerator.

An alternative technique which is becoming increasingly popular is to use a particle accelerator of a weight and size which permit the particle accelerator itself to be mounted to a support, such as a gantry, to permit movement e.g. rotation of the accelerator and hence the output beam of charged particles. In such arrangements the support may be rotatable to permit rotation of the particle accelerator and coil about the axis of the coil. One type of particle accelerator which may be constructed to be sufficiently lightweight and compact to enable mounting to a support for rotation is a particle accelerator including one or more superconducting coils. Such coils may generate a more intense magnetic field than may be achieved using a comparable size particle accelerator which does not include a superconducting coil enabling a reduction in size and weight to be achieved. For example, a superconducting wire of relatively small cross-section may carry very high electric currents, in the order of hundreds or thousands of amperes without dissipation. Current densities one hundred times greater than those typically achieved using resistive coils may be obtained without difficulty.

Support mounted particle accelerators are advantageous in that they may provide beam directing capability in the context of a smaller and cheaper installation. This is particularly important, for example in the context of ion therapy applications, enabling treatment installations to become more widespread, potentially allowing treatment centres to be located at a district rather than regional or national level.

When a particle accelerator including a superconducting coil is used, it is necessary to cool the superconducting windings. It will be appreciated that particular problems are encountered when cooling the superconducting coil of a particle accelerator mounted to a support for rotation. The cooling system should permit the particle accelerator to be mounted to the support, and be operable to cool the coil even upon rotation of the particle accelerator and its coil.

Various methods for cooling coils of superconducting systems have been proposed. Some conventional cooling methods for superconducting coils involve immersing the coil in a liquid cryogenic coolant or "cryogen". The cryogen most commonly used is liquid helium. The cryogen absorbs heat from the superconductor, and is vaporised, thus cooling the superconductor. However, the need to immerse the superconductor in the cryogen has certain drawbacks, particularly in the context of a support mounted rotatable particle accelerator system. One of the most significant problems associated with immersing the superconducting coil in a cryogen bath is that this results in a relatively bulky system, not well suited to mounting to a support, or to rotation. Due to the relatively large quantities of cryogen required, it is generally necessary that the cryogen containing bath is a pressure vessel, capable of withstanding the potentially high pressures which may result from vaporisation of the cryogen on quenching of the superconducting magnet. Quenching is a phenomenon which may occur if the superconducting magnet comes out of its superconducting state and enters a resistive state. This may result in the release of energy from the coil in the form of heat, causing cryogen surrounding the coil to vaporise. Furthermore, it is likely that cryogens, such as liquid helium, will become increasingly scarce in the future, making immersion systems which use large quantities of cryogen less desirable.

Other known cooling methods use thermal conductors, such as copper thermal links, to transfer heat from the superconducting coil to the working fluid of a cryocooler, without using a cryogen as a heat transfer medium. However, these systems also have certain drawbacks. For example, significant temperature gradients may arise over the length of the conductors, degrading performance of the superconducting coil. A further problem arises, as cryocoolers generate vibration which may interfere with the operation of a particle accelerator. Conversely, the strong magnetic fields produced by a particle accelerator may interfere with the operation of the cryocooler. In order to avoid interference between the cryocooler and particle accelerator, it is necessary to locate the cryocoolers at a distance from the superconducting coils of the particle accelerator. However, in practice, there are practical difficulties associated with conducting heat over significant distances. Thus, the Applicant has realised that such systems are also not well suited to maintaining the temperature of the superconducting coil low and stable, as is desirable to maintain effective operation of a particle accelerator.

The Applicant has therefore realised that there is a need for an improved cooling method and system for the superconducting system of a particle accelerator mounted to a support to permit changing e.g. rotation of the direction of the output beam.

In accordance with a first aspect of the invention there is provided;
a system comprising:
a support; and
a particle accelerator mounted to the support for producing an output beam of charged particles in use, the particle accelerator comprising at least one annular superconducting coil for generating a magnetic field in use;
the system further comprising means for cooling the superconducting coil in use;
the cooling means comprising:
a cryogen chamber which is situated local to the at least one superconducting coil for containing cryogen in use;
thermally conductive means arranged to facilitate heat transfer from the at least one superconducting coil to the cryogen chamber to vaporize cryogen contained therein in use and thereby remove heat from the at least one superconducting coil, the thermally conductive means being highly thermally conductive at cryogenic temperatures;

and a cryogen recondensing unit in fluid communication with the cryogen chamber, whereby vaporized cryogen may flow from the cryogen chamber to the cryogen recondensing unit to be recondensed in use before returning to the cryogen chamber;

wherein the system is arranged such that the particle accelerator is movable to change the direction of the output beam in use with rotation of the at least one superconducting coil about its axis, and wherein the cooling means is operable to cool the superconducting coil as the coil rotates about its axis upon said movement of the particle accelerator in use.

In accordance with the invention, therefore, a cryogen chamber is provided local to the superconducting coil of the particle accelerator. A liquid cryogen located in the chamber in use may absorb and be vaporised by heat transmitted to it from the superconducting coil to thereby cool the coil. Highly thermally conductive means is specifically provided to facilitate transfer of heat from the superconducting coil to the cryogen chamber to vaporise cryogen located therein in use. The present invention thus uses a thermal conduction path to transfer heat from the superconducting coil to cryogen located in a cryogen chamber in the vicinity of coil in use. The cryogen chamber is in fluid communication with e.g. connected to a cryogen recondensing unit, whereby in use, cryogen located in the chamber and vaporised by heat from the superconducting coil may flow to the cryogen recondensing unit to be recondensed before returning to the chamber. The recondensed cryogen may then be vaporised once more to start a new cycle.

In this way, the present invention provides a cooling system for the superconducting coil or coils of the system, in which heat is extracted from the coil or coils in a two step process. First of all, heat is transmitted by thermal conduction over the relatively short distance to a local cryogen chamber to vaporise cryogen present in the chamber in use. In the second stage, the vaporised cryogen acts as a heat transfer medium to remove heat from the vicinity of the superconducting coil, travelling from the cryogen chamber to a recondensing unit.

It has been found that the combination of the two different heat transfer mechanisms, i.e. using the cryogen in its vaporised state as a heat transport medium only in the latter stages of the cooling process to transport heat to the recondensing unit, e.g. over the longer range, with thermal conduction via specific highly thermally conductive means being used to initially transmit heat from the coil to the cryogen, i.e. over the shorter range, is particularly advantageous in the context of the superconducting coil of a support mounted particle accelerator, allowing the present invention to address problems associated with both prior art arrangements which rely upon immersion of the coil in a cryogen bath to remove heat from the coil, and those which rely upon the use of thermal conductors to transmit heat over a significant distance directly to the working fluid of a heat pump, such as a cryocooler, without using a cryogen.

In contrast to immersion type arrangements, the present invention allows a significantly smaller quantity of cryogen to be used, and corresponding reductions in the size of the cryogen chamber to be obtained in comparison to prior art cryogen baths. This may result in a lighter weight and more compact system, which is suited to mounting on a support.

The ability to use a smaller quantity of cryogen in comparison to immersion type arrangements, is a result of the presence of thermally conducting means dedicated to facilitating transmission of heat from the coil to the interior of the cryogen chamber to vaporise cryogen, and a recondensing unit for recondensing the vaporised cryogen. The presence of the highly thermally conductive means allows the temperature of the coil to be maintained close to the temperature of the liquid cryogen without needing to provide a substantial quantity of cryogen adjacent the coil in a cryogen bath to act as a cold reservoir. In accordance with the invention, immersion of the coil in cryogen is replaced by thermal contact of the coil with highly thermally conductive means arranged to transmit heat to the cryogen chamber. As the arrangements of the present invention no longer require the coil to directly contact the cryogen, the potential pressures which may arise during quenching of the coil may be reduced, as the time taken for heat generated in a quench to reach the cryogen is increased, resulting in heat being transferred over a longer period. This may allow greater flexibility in the construction of the cryogen chamber, which need not be designed to withstand such high pressures as a conventional cryogen bath. Furthermore, by reducing the size of the cryogen chamber relative to a conventional cryogen bath, and providing highly thermally conductive means to transport heat to the chamber, greater flexibility in the construction of the overall system, e.g. its size and configuration is provided, as the cryogen does not need to be in direct contact with the coils.

As the cryogen chamber is local to the superconducting coil, the distances over which heat must be transmitted by thermal conduction are relatively small in use, reducing the quantity of thermally conductive material required, and avoiding problems associated with thermal losses and temperature gradients which may occur when heat is transmitted over a longer range e.g. directly to a cryocooler of a recondensing unit using thermal links. This may enable the superconducting coil to be maintained more readily at a suitable temperature to ensure reliable operation of the particle accelerator. In accordance with the invention, heat need only be transmitted as far as the local cryogen chamber by conduction to enable it to vaporize the cryogen in use, with the vaporised cryogen then being used to transport heat away from the vicinity of the coil, e.g. to a cryocooler if desired. The use of vaporised cryogen as the heat transport medium over the longer range to a recondensing unit, may allow heat be conveniently transferred over relatively great distances, as the mass and size of apparatus required to transport heat over a given distance using vaporised cryogen is very much smaller than would be required to transport a corresponding quantity of heat using a solid thermal link of e.g. copper. This allows the recondensing unit to be located at greater distances from the cryogen chamber than prior art arrangements permit, without compromising efficiency of the cooling system to a detrimental degree.

By removing the constraints on the distance at which the coil may be located relative to the recondensing unit, the present invention may allow superconducting coils providing stronger magnetic fields to be used, as the recondensing unit may be located at a sufficiently great distance from the coil to avoid unacceptable interference with its operation by the coil or other parts of the particle accelerator. It is desirable to be able to use superconducting magnets which provide stronger magnetic fields, as these enable the overall size of the magnet, and hence particle accelerator to be reduced, resulting in a more compact apparatus for support mounting. In embodiments of the invention, the recondensing unit may be located in a relatively low magnetic field region. Furthermore, the use of the cryogen for transporting heat to the recondensing unit has been found to allow better vibration isolation to be obtained between the coil and recondensing unit, which may include a motor and other moving parts, reducing the likelihood that the cooling system may interfere with operation of the particle accelerator.

It should be appreciated that all references to thermal conductivity herein, unless stated otherwise, refer to thermal conductivity at cryogenic temperatures. Cryogenic temperatures may be taken to be temperatures of less than 100 K, and thus, the highly thermally conductive means is highly thermally conductive at cryogenic temperatures in the range of less than 100K. As discussed below, the highly thermally conductive means is highly thermally conductive over at least some temperatures within the range of cryogenic temperatures, and need not be highly thermally conductive over the entire range of less than 100K depending upon factors such as the temperature of operation of a given system, the cryogen used etc. In typical embodiments, the cryogenic temperatures at which the system is operated may be less than 40K, or less than 10K.

Accordingly, it will be appreciated that the present invention may address some of the conflicting problems encountered when designing a cooling system for the superconducting coil of a particle accelerator mounted to a support, and which is arranged to be movable with rotation of the coil about its axis in use for movement of an output beam of the accelerator. The present invention eliminates the need to provide a conventional bath of cryogen for immersing the coil, but still provides a chamber containing cryogen which is located local to the coil, providing the ability to cool the coil in a manner which may ensure reliable operation of the particle accelerator. The present invention may allow cooling to low, stable temperatures to be achieved, which is desirable, particularly in the context of certain superconducting coil materials which are associated with higher magnetic field strengths.

It will be appreciated that, in use, the particle accelerator is movable so as to permit movement of the output beam, preferably through an arc in use. The particle accelerator is rotatable (about an axis of rotation) with corresponding rotation of the superconducting coil of the particle accelerator about the coil axis. In embodiments the particle accelerator and coil have a common axis. In accordance with the invention, the cooling means is arranged such that is capable of cooling the coil as the superconducting coil rotates about the axis of the coil upon movement of the particle accelerator. Thus the cooling means may continue to cool the coil as the coil rotates through a range of angular positions about its axis.

In accordance with the invention, the cooling means is arranged to cool the coil as the coil rotates about its axis in use. Thus, the cooling means is arranged to rotate with the coil as it rotates about its axis in use. In preferred embodiments, the cryogen chamber, thermally conductive means and recondensing unit all rotate with the coil. The cooling means is therefore mounted to the support. In these embodiments, the cryogen chamber, thermally conductive means and recondensing unit rotate as a unit with the particle accelerator and superconducting coil. In preferred embodiments the particle accelerator including the superconducting coil and cooling means define a single unit which is mounted to the support. In embodiments, the particle accelerator comprises the cooling means.

The particle accelerator and support may be arranged in any manner to result in movement of the particle accelerator for movement of the output beam such that the coil rotates about its axis in use. It will be appreciated that the coil axis is the axis about which the at least one annular superconducting coil circumferentially extends.

In some embodiments, the particle accelerator is rotatably mounted to the support in order to change the direction of the output beam, e.g. to rotate the output beam through an arc. The particle accelerator is then rotatable in a manner which results in the coil rotating about the coil axis in use. In these embodiments the particle accelerator may directly rotate about an axis of rotation corresponding to the axis of the coil. In some embodiments the particle accelerator may rotate about an axis of the support to which it is mounted. Preferably the particle accelerator is arranged to rotate about a horizontal axis.

In embodiments in which the particle accelerator is rotatably mounted to the support, the particle accelerator may be rotatably mounted to the support using bearings. The support may be in the form of an arm, and the particle accelerator may be rotatably mounted to an end of the arm. The axis of rotation of the particle accelerator may correspond to an axis of the arm.

Alternatively or additionally, the support is a rotatable support, and the support is arranged to rotate about a support axis of rotation in order to rotate the particle accelerator and output beam through a range of rotational positions with rotation of the coil about its axis. In these preferred embodiments, the particle accelerator is mounted to the support such that it will rotate with the support in use about the support axis of rotation to change the direction of a beam of charged particles output by the particle accelerator. These arrangements are preferred as they may result in movement of the output beam through a greater range of angles as a result of the physical displacement of the particle accelerator as it rotates. The beam may be centred on the same target, or isocenter, as it is rotated. In these embodiments, as the particle accelerator including the coil is mounted to the support, rotation of the support about its axis of rotation will result in rotation of the superconducting coil about its axis. This will allow rotation of the particle accelerator and hence coil to enable movement of the output beam through an arc even if the particle accelerator is not movable relative to the support (although the particle accelerator may additionally be e.g. rotatably mounted to the support as discussed below).

In accordance with a further aspect of the invention there is provided;

a system comprising:

a support rotatable about a support axis of rotation in use; and a particle accelerator mounted to the support for producing an output beam of charged particles in use, the particle accelerator comprising at least one annular superconducting coil for generating a magnetic field in use, wherein the particle accelerator is mounted to the support such that it will rotate with the support in use about the support axis of rotation to change the direction of a beam of charged particles output by the particle accelerator;

the system further comprising means for cooling the superconducting coil in use;

wherein the cooling means comprises:

a cryogen chamber situated local to the at least one superconducting coil for containing cryogen in use;

thermally conductive means arranged to facilitate heat transfer from the at least one superconducting coil to the cryogen chamber to vaporize cryogen contained therein in use and thereby remove heat from the at least one coil, the thermally conductive means being highly thermally conductive at cryogenic temperatures;

and a cryogen recondensing unit in fluid communication with the cryogen chamber, whereby vaporized cryogen may flow from the cryogen chamber to the cryogen recondensing unit to be recondensed in use before returning to the cryogen chamber;

and wherein the cooling means is operable to cool the superconducting coil as the coil rotates about its axis upon rotation of the particle accelerator with the support in use.

The present invention in accordance with this further aspect of the invention may include any or all of the features described with respect to the other aspects and embodiments of the invention to the extent that they are not mutually inconsistent therewith.

In embodiments of the invention in which the particle accelerator is mounted to a rotatable support for rotation with the support about a support axis of rotation, whether or not the particle accelerator is rotatably mounted thereto, the axis of rotation of the support may correspond to the axis of the coil. However, in preferred embodiments, the axis of rotation of the support and the axis of the coil are different.

In preferred embodiments the support is arranged to rotate about an axis of rotation which is parallel to the axis of the coil (and particle accelerator).

Preferably the support is rotatable about a horizontal axis of rotation.

Preferably the particle accelerator is mounted to the support such that the axis of the superconducting coil is horizontal. In these embodiments, the coil therefore rotates about a horizontal coil axis as the support rotates about the support axis.

In accordance with any of the aspects and embodiments of the invention in which the (particle accelerator) support is rotatable, the particle accelerator support may be of any suitable type. For example the support may comprise an arm pivotable about an axis of rotation. The particle accelerator may then be mounted to an end of the arm remote from the axis of rotation. The arm may be an articulated arm allowing movement of the particle accelerator about one or more axes.

However, in preferred embodiments of the invention, the support is a gantry rotatable about a gantry axis of rotation, and the particle accelerator is therefore a gantry mounted particle accelerator. In preferred embodiments in which the particle accelerator is mounted to an arm of the gantry, the arm is preferably rotatable about a gantry axis of rotation parallel to the axis of the arm. Preferably the particle accelerator is mounted to the arm such that the axis of the superconducting coil (and the particle accelerator) is parallel to, or coincides with the axis of the arm.

In embodiments in which the particle accelerator is gantry mounted, the gantry may be of any suitable form. In preferred embodiments, the gantry comprises an arm extending between a pair of legs which extend from the axis of rotation of the gantry, and the particle accelerator is mounted to the arm. The arm will then extend parallel to the gantry axis of rotation. The arm may be defined by one or more axially extending members. In these embodiments the gantry is bridge like. Such arrangements may be advantageous in that they are more space efficient, requiring less space to accommodate the gantry structure. The particle accelerator may additionally rotate about the axis of the arm.

In accordance with any of the aspects or embodiments of the invention, while the particle accelerator is movable with the result that the coil rotates about its axis, the particle accelerator may additionally be movable in one or more other directions, and may be rotatable about a plurality of axes.

In accordance with any of the aspects or embodiments of the invention in which the particle accelerator is mounted to a rotatable support, the particle accelerator may or may not be arranged to rotate about another axis of rotation as it rotates with the support about the support axis of rotation.

Thus, while in some embodiments the particle accelerator may be non rotatably mounted to a rotatable support, and may be non movably mounted thereto, with rotation of the coil about its axis occurring as a result of rotation of the particle accelerator with the support about the support axis, in other embodiments, it is envisaged that the particle accelerator may be movably mounted to such a rotatable support to increase the range of movement of the particle accelerator and hence the direction of the output beam. Thus, in some embodiments, the particle accelerator is arranged to rotate about another axis as it rotates with the support about the axis of rotation of the support. The other axis may be in any desired orientation to result in appropriate direction of the output beam. The particle accelerator may additionally be rotatably mounted to the support in any of the manners discussed above. For example, the particle accelerator may be arranged to additionally rotate about an axis of the support, preferably a horizontal axis thereof.

In accordance with any of the aspects or embodiments of the invention, whether the particle accelerator is mounted to a rotatable support or not, and whether or not the particle accelerator is rotatably mounted, the particle accelerator may be arranged such that in use it is movable with resultant tilting of the coil axis. These arrangements may further increase the range of available direction for the output beam. The particle accelerator may be arranged to move so as to result in movement of the axis of the coil out of a horizontal plane. The particle accelerator may be arranged to move with resultant tilting of the coil axis through an angle of up to 20 degrees, preferably in the range of from 5 to 15 degrees in one or both directions from a position in which the coil axis lies in a horizontal plane. This may be achieved, for example, using an arrangement of gimbals.

In accordance with any of the aspects and embodiments of the invention, regardless of the way in which the particle accelerator and support are arranged to result in movement of the particle accelerator with rotation of the coil, the particle accelerator may be rotatable through any range of angles with corresponding rotation of the coil about its axis while the cooling means is operable i.e. capable of cooling the coil. The range of angles will depend upon the intended application. Preferably the cooling means is operable to cool the coil as the coil rotates through at least 90 degrees, more preferably at least 160 degrees, and in some embodiments through at least 170 degrees about its axis. The cooling means is therefore operable to cool the coil as the particle accelerator rotates through an angle in any of the above ranges with rotation of the coil about its axis. In preferred embodiments the cooling means is operable to cool the coil as the coil rotates through up to 180 degrees, and preferably through an angular range of from 90 to 180 degrees about its axis. In embodiments in which the particle accelerator is mounted to a rotatable support, the support is rotatable through a corresponding range, of angles to permit rotation of the particle accelerator and coil through the above range of angles.

In preferred embodiments, the beam is movable through an arc as the particle accelerator moves i.e. rotates. The beam may move through any part of a circle as the particle accelerator is rotated. For example, movement of the particle accelerator may result in the beam moving through an arc describing an upper part of a circle or a left or right side of a circle. In some embodiments, the particle accelerator may be moved through 180 degrees between a rotational position in which the emitted beam moves in a first horizontal direction toward a target, and a position in which the beam moves in a second opposed horizontal direction toward the target. In other embodiments, the particle accelerator may be moved through 180 degrees between a rotational position in which the emitted beam moves in a first vertical direction toward a target, and a position in which the beam moves in a second opposed vertical direction toward the target.

In accordance with any of the aspects and embodiments of the invention, preferably the system is arranged such that recondensed cryogen returns under the action of gravity to the cryogen chamber. In these embodiments, the recondensed cryogen returns to the cryogen chamber under the action of gravity over the range of rotation of the coil with the cooling means being operable to cool the coil. In these preferred embodiments the range of rotation of the particle accelerator and hence coil with the cooling means operable to cool the coil may be constrained only by the requirement that the recondensed cryogen is able to return from the recondensing unit to the cryogen chamber under the action of gravity. In embodiments, the system is arranged such that the cooling means is operable to cool the superconducting coil as the coil is rotated about its axis through a range of rotational positions in which cryogen may return from the recondensing unit to the cryogen chamber under the action of gravity, and preferably through the entire range of such positions.

In embodiments, the particle accelerator comprises a beam outlet for outputting a beam of charged particles in use. The beam outlet may be a nozzle. The beam outlet may be arranged such that the beam emerges tangential to the particle accelerator. It will be appreciated that in use, rotation of the particle accelerator with rotation of coil about its axis will result in rotation of the beam thereby changing the direction of travel of the output beam. The beam may be a straight line beam.

Preferably the system further comprises an source for supplying charged particles to the particle accelerator for acceleration.

In embodiments the particle accelerator is arranged to produce an output beam of charged particles which is directed towards a target. Preferably the particle accelerator is arranged such that upon rotation of the particle accelerator, the output beam is incident upon a given target from a plurality of directions, and preferably moves through an arc centred on the target. This may enable irradiation of the given target from a plurality of directions. The target may provide an isocenter for the beam. As described above, in preferred embodiments, the beam may be moved through an angle of up to 180 degrees as the particle accelerator rotates, and thus in preferred embodiments, the beam is arranged to be incident upon a given target as it is moved through an angle of up to 180 degrees. In these preferred embodiments, the beam passes through the target as it moves through an arc. In preferred embodiments in which the particle accelerator is mounted to a rotatable support, the target is a point on, or in the plane of, the axis of rotation of the support.

The particle accelerator may be used in conjunction with any type of charged particle. In preferred embodiments the charged particles are protons or so called heavy ions, such as carbon.

In accordance with these embodiments of the invention, the charged particle therapy system may be an ion e.g. heavy ion or proton therapy system. In preferred embodiments, the system is a system for delivering charged particle therapy in use.

It is known that when high energy charged particles travel through matter, they deposit their energy in a non-uniform way. This is because the strength of their interaction with matter ("the interaction cross section") increases as the particles lose energy. This effect gives rise to a "Bragg peak", whereby the majority of the particle's energy is deposited at a particular depth inside the target. This is in contrast to the behaviour of high energy photons, such as X-rays, with which greater deposition of energy occurs close to the surface of the target, with an exponentially decreasing dose inside the target. The existence of this "Bragg Peak" is increasingly being exploited in new forms of radiotherapy known as "Proton" or "Heavy Ion" therapy. Heavy Ion therapy may use ions such as carbon. This is because the Bragg Peak effect allows a radiation dose to be more effectively targeted on deep seated objects, e.g. tumours, while reducing the radiation dose to surrounding healthy tissues. It is particularly desirable, therefore, to use a particle accelerator to deliver therapy, by directing charged particles upon a target in a body.

The system of the present invention allows the output beam of the particle accelerator to be rotated in order to be incident upon a target from a range of angles. This is particularly advantageous in the context of ion therapy, allowing the dose to non target e.g. healthy surrounding tissue to be further reduced. As the particle accelerator is mounted to a support to permit rotation of the particle accelerator, this may be achieved without requiring a change in the orientation of the patient with respect to gravity. This is desirable, as the internal organs are liable to move under the influence of gravity, and the patient should therefore remain in a constant position with respect to gravity throughout treatment. As the present invention uses a support mounted rotatable particle accelerator, and is arranged such that cooling of the superconducting coil of the accelerator may be achieved effectively even as the accelerator and coil rotate, this enables the system to be installed relatively cost effectively and in a smaller space than would be required using a static particle accelerator, and using beam steering systems to transmit the beam to a patient, and direct it upon a target from different directions. This makes the system suitable for use even on a district hospital type scale, improving accessibility of treatment.

It will be appreciated that in these embodiments, the system may be used to deliver therapy to a human or non-human animal body, and references to a "Patient" should be understood to refer to a non human or human body.

In these embodiments the particle accelerator is arranged to direct the output beam upon a target to be irradiated from a plurality of directions as the particle accelerator rotates. The target will correspond to a point on or in a patient to be treated in use. As described above, in embodiments, the target may be a point in the plane of, or on the axis of rotation of the support.

Preferably the system further comprises a patient support, and the particle accelerator is arranged to direct an output beam toward a target in the region of the patient support as it rotates.

In accordance with a further aspect of the invention, there is provided a system for delivering charged particle therapy in use, the system comprising:
    a patient support;
    a particle accelerator support; and
    a particle accelerator mounted to the particle accelerator support and being arranged to output a beam of charged particles towards a target in the region of the patient support in use, the particle accelerator comprising at least one annular superconducting coil for generating a magnetic field in use;
    the system further comprising means for cooling the superconducting coil in use;
    the cooling means comprising:
    a cryogen chamber which is situated local to the at least one superconducting coil for containing cryogen in use;

thermally conductive means arranged to facilitate heat transfer from the at least one superconducting coil to the cryogen chamber to vaporize cryogen contained therein in use and thereby remove heat from the at least one coil, the thermally conductive means being highly thermally conductive at cryogenic temperatures;

and a cryogen recondensing unit in fluid communication with the cryogen chamber, whereby vaporized cryogen may flow from the cryogen chamber to the cryogen recondensing unit to be recondensed in use before returning to the cryogen chamber;

wherein the system is arranged such that the particle accelerator is movable to change the direction of the output beam in use, and wherein the cooling means is operable to cool the superconducting coil as the coil rotates about its axis upon said movement of the particle accelerator in use.

In accordance with yet another aspect of the invention there is provided a system for delivering charged particle therapy in use, the system comprising:

a patient support;

a particle accelerator support rotatable about a particle accelerator support axis of rotation in use, and a particle accelerator comprising at least one annular superconducting coil for generating a magnetic field in use, the particle accelerator being arranged to output a beam of charged particles towards a target in the region of the patient support in use, and being mounted to the particle accelerator support such that the particle accelerator will rotate with the particle accelerator support to change the direction of the output beam of charged particles in use;

the system further comprising means for cooling the superconducting coil in use;

and wherein the cooling means comprises:

a cryogen chamber which is situated local to the at least one superconducting coil for containing cryogen in use;

thermally conductive means arranged to facilitate heat transfer from the at least one superconducting coil to the cryogen chamber to vaporize cryogen contained therein in use and thereby remove heat from the at least one coil, the thermally conductive means being highly thermally conductive at cryogenic temperatures;

and a cryogen recondensing unit in fluid communication with the cryogen chamber, whereby vaporized cryogen may flow from the cryogen chamber to the cryogen recondensing unit to be recondensed in use before returning to the cryogen chamber;

and wherein the cooling means is operable to cool the superconducting coil as the coil rotates about its axis upon rotation of the particle accelerator with the particle accelerator support in use.

The present invention in accordance with these further aspects may comprise any or all of the features described in relation to the other aspects and embodiments of the invention, to the extent that they are not inconsistent therewith.

In accordance with these further aspects and embodiments of the invention, the target will be chosen in use to correspond to a target in or on the patient to be irradiated. In some embodiments the target is a point on or in the patent support. This may result in the beam passing through a patient located on the patient support in use. In some embodiments in which the system comprises a patient support, the longitudinal direction of the patient support is parallel to, and preferably coincides with an axis of rotation of the support to which the particle accelerator is mounted. The patient support may be a horizontal support.

It will be appreciated that rotation of the particle accelerator either directly and/or through movement of a support to which it is mounted such that the coil rotates about its axis will result in movement of the output beam through an arc. As discussed above, the particle accelerator may be arranged to rotate through any suitable angle to move the beam through an angle appropriate for a given therapy with the cooling means operating to cool the coil. It has been found that rotation of the support through 180 degrees is generally sufficient to irradiate a target in a supine patient on the patient support from all directions. In some embodiments, the beam may be rotatable from a position in which the output beam moves vertically downward to be incident upon a target (in the patient) in use to a position in which it moves vertically upward to be incident upon the target. In other embodiments, the beam may be rotatable from a position in which it moves horizontally in a first direction to be incident upon a target (in the patient) in use to a position in which it moves horizontally in a second opposed direction to be incident upon a target in the patient in use. Of course, the particle accelerator may be moved through any other range of angles, and may move through any intervening range of positions, or through any greater range of positions.

In some embodiments the patient support is arranged to be rotatable about at least one patient support axis of rotation. The patient support may be arranged to rotate about one or more axes. In this manner, the patient support may be arranged to rotate as the particle accelerator rotates. This may increase the range of angles at which the output beam may be incident upon the target for a given range of rotation of the particle accelerator support. This may reduce the angle through which the particle accelerator need be rotated providing a more space efficient arrangement. It will be appreciated that a part of the surroundings of the patient support e.g. a floor etc may rotate with the patient support about the patient support axis.

In some embodiments, the patient support is arranged to rotate about a vertical axis. Alternatively or additionally, the patient support may be arranged to rotate about a horizontal axis. The patient support may therefore be arranged to counterrotate about one or more axes which may, for example be vertical and/or horizontal axes as the particle accelerator rotates with rotation of the coil about its axis. In some embodiments, in which the particle accelerator is mounted on a support rotatable about a support axis of rotation, the system may further comprise a counterweight rotatable about the support axis of rotation in the opposite sense as the support rotates. In some embodiments, the patient support is rotatable with the counterweight about the support axis of rotation. In these embodiments, the patient support and particle accelerator counter-rotate about an intermediate axis.

It will be appreciated that in accordance with the present invention, the superconducting coil is a coil of a superconducting magnet, and the superconducting coil is arranged to provide a magnetic field when current flows through its windings.

The present invention may be applied to high temperature or low temperature superconducting systems. In superconducting systems the superconducting coil of the system must be operated at a temperature at or below a critical temperature in order to be able to achieve and/or maintain superconductivity. The invention is particularly applicable to so-called "low temperature" superconducting systems. Lower temperature superconducting systems may be advantageous for use in the context of a support mounted particle accelerator, as they may provide stronger magnetic fields per unit mass, allowing a reduction in the amount of wire needed to form the superconducting coil, and hence of the overall mass and size of the particle accelerator. Critical temperatures for low temperature superconductors are in the cryogenic order, typically of, for example, less than 20K. For example, niobium titanium (NbTi) and niobium tin ($Nb_3Sn$), which are superconducting materials commonly used in low temperature superconducting systems, have superconducting transition temperatures of 10.1K and 18.5K respectively. To provide adequate superconducting performance, superconductors comprising these materials must be cooled to well below these critical transition temperatures, e.g. to allow superconducting coil of a supermagnet to be able to carry large current densities in the presence of high magnetic fields.

In accordance with the invention in any of its aspects and embodiments, the at least one superconducting coil may be of any size. It is desirable for the coil to be made as small as possible in order to reduce the weight that must be supported for rotation by the support.

The coil may be formed of any suitable material which is superconducting at low e.g. cryogenic temperatures. Preferably the at least one coil comprises niobium titanium and/or niobium tin. The superconducting material e.g. niobium titanium and/or niobium tin may be embedded in a composite metallic matrix as is well known in the art.

While the invention has been described in detail in respect of one superconducting coil, it will be appreciated that the system may comprise any number of coils, and, if not explicitly stated, references to "the coil" should be understood to refer to "the at least one coil", and this may be the, each or a coil, where a plurality of coils are present. The second or any further coil may be of the same construction as the first, and may include any or all of the features described in respect of the first coil. Preferably the particle accelerator comprises a pair of superconducting coils spaced from one another along a common axis of the coils.

In accordance with the invention, heat is transferred by conduction between the cryogen located in the cryogen chamber in use, and the superconducting coil, via highly thermally conductive means. Any material having a suitably high level of thermal conductivity at cryogenic temperatures may be used to provide the highly thermally conductive means, and examples of suitable materials are known in the art. The highly thermally conductive means may comprise one or more different materials, which may be of the same or different thermal conductivity, provided that any composite exhibits high levels of thermal conductivity. Preferably the highly thermally conductive means comprises or consists of a metal. For example, the highly thermally conductive means may comprise aluminium. However, in particularly preferred embodiments the highly thermally conductive means comprises or consists of copper.

The highly thermally conductive means typically has a higher thermal conductivity than materials conventionally used to provide structural components in conventional supermagnet systems. Such materials typically have a low thermal conductivity at cryogenic temperatures of less than 10 W/m/K, and include materials such as stainless steel, aluminium alloy, or glass reinforced polyester. The highly thermally conductive means therefore has a high thermal conductivity relative to stainless steel.

Preferably the highly thermally conductive means has a thermal conductivity in the range of greater than 100 W/m/K at cryogenic temperatures, and more preferably greater than 200 W/m/K. As described above, references to cryogenic temperatures herein refer to temperatures of less than 100K, and the highly thermally conductive means should be highly thermally conductive at temperatures over at least a part of this range. For example, if the superconducting coil is a low temperature superconductor, it may only be necessary for the thermally conductive means to be highly thermally conductive over the lower part of the above temperature range corresponding to the operating temperature range of the system. In practical terms, the lowest temperatures likely to be encountered would be in the order of 4K. In preferred embodiments, the highly thermally conductive means has a high thermal conductivity at temperatures over at least a part of a range of from 4K to 10K, and preferably over the entire range. This range has been found to be particularly appropriate when the cryogen used is helium. The appropriate range over which high thermal conduction properties are exhibited may be selected as desired for a given application and arrangement to result in suitable operation of the system, and may depend upon factors such as the type of cryogen used. For example, the properties may be exhibited at temperatures of up to 50K or greater, depending upon the temperature of operation of the system.

Any other ranges for thermal conductivity described herein, e.g. with reference to other components of the system, should similarly be taken as being with reference to such properties being exhibited at such cryogenic temperatures. It will be appreciated that the "highly thermally conductive means" may, for brevity, be referred to the "thermally conductive means" below.

Preferably the highly thermally conductive means has a thermal conductivity in the range of greater than 100 W/m/K at room temperature.

The thermally conductive means may be of any form and arranged in any manner to facilitate transfer of heat by thermal conduction between the coil and cryogen located in the cryogen chamber in use. For example, the thermally conductive means may comprise one or more thermally conductive connectors, and/or thermally conductive layer(s).

The thermally conductive means may extend the entire distance between the at least one coil and the interior of the cryogen chamber. In this way, the thermally conductive means may provide a direct thermal conduction path between a surface of the coil and the interior of the cryogen chamber in order to be able to directly contact cryogen located in the chamber in use. Preferably the thermally conductive means is arranged to directly contact a surface of the coil at one end thereof, and to directly contact cryogen located in the cryogen chamber in use at the other end thereof. The thermally conductive means may extend along any suitable path or paths between the coil and cryogen chamber, and may extend through or around any intervening layers.

The thermally conductive means may be arranged to transmit heat between the coil and the cryogen chamber at only a selected point or points of a surface area of the coil, or at a plurality of points, which may be in the form of a continuous or discontinuous area. In some embodiments, the thermally conductive means may be arranged to collect heat from different parts of the coil and to deliver the heat to the cryogen chamber. In this manner, the thermally conductive means may transport heat from parts of the coil which are not directly or indirectly adjacent the cryogen chamber, or at least to a cryogen containing part thereof, to cryogen in the chamber in use.

Preferably the thermally conductive means is segmented at least in the region contacting the coil. This may help to avoid the generation of significant eddy currents in the thermally conductive means.

It will be appreciated that in effect, the present invention replaces cryogen provided in a cryogen bath arranged adjacent the coil in order to immerse the coil with the thermally conducting means which contacts the coil to remove heat therefrom and transfer it to a cryogen chamber, providing greater flexibility in the location and size of the cryogen chamber relative to the coil. The greater the area of contact between the coil and the thermally conductive means, the greater the efficiency with which heat may be extracted from the coil.

In preferred embodiments, the thermally conducting means is in thermal contact with a substantial portion of the surface area of the coil. In embodiments, the thermally conductive means extends around at least portion of a circumference of the coil. In this way, heat may be extracted directly from a greater portion of the coil to increase the rate of cooling. Preferably the thermally conductive means is arranged to be in contact with the coil over at least 25%, more preferably at least 50%, and most preferably at least 75% of a circumference of the coil, and in some embodiments the thermally conductive means contacts the coil around substantially the entire circumference thereof. In these embodiments, the thermally conducting means may contact a radially outer surface of the coil. In some preferred embodiments the thermally conductive means is in contact with an axial end of the coil. This may enable the thermally conductive means to extend around an axial end of an external coil support, where provided, to contact the cryogen chamber.

The extent to which the thermally conductive means extends relative to the interior surface of the cryogen chamber should be chosen to allow the thermally conductive means to facilitate the transfer of heat to the interior of the chamber in some manner even on rotation of the coil. As the present invention allows the size of the cryogen chamber and volume of cryogen present to be significantly reduced relative to prior art arrangements which rely on immersion of the coil or coils in cryogen, heat may more readily be transferred to any cryogen present within the limited area of the cryogen chamber. The way in which the thermally conductive means is arranged relative to the cryogen chamber may be selected as appropriate depending upon factors such as the size of the cryogen chamber, distance between the cryogen chamber and the coil, and quantity of cryogen located in the chamber in use to achieve a desired level of heat transfer. The thermally conductive means may penetrate a wall of the cryogen chamber, or, in some embodiments, it is envisaged that the thermally conductive means may at least partially define a wall of the cryogen chamber.

In preferred embodiments, the thermally conductive means may be arranged to distribute heat from one part of the cryogen chamber to another. The parts are different regions around the circumference of the chamber. The thermally conductive means may therefore be arranged such that it may conduct heat from a part of the cryogen chamber which does not contain cryogen in use to a part of the chamber which does contain cryogen. The thermally conductive means is preferably arranged such that it may conduct heat from a part of the cryogen chamber which does not contain cryogen in use to a part of the chamber which does contain cryogen as the coil and cryogen chamber rotate. In use, cryogen in the cryogen chamber will flow around the chamber as the coil rotates. Thus, for example, if the cryogen initially fills the cryogen chamber to half its height, and the cryogen chamber extends around the entire circumference of the coil axis (or preferably coil), if the chamber and coil are rotated though 90 degrees in either direction, each point within the cryogen chamber will at some point be in contact with cryogen, and at some point not be in contact with cryogen. The thermally conductive means is preferably arranged to provide a path for distributing heat from a region of the chamber which is not in contact with cryogen to a part which is in contact with cryogen over the full range of rotation of the system, preferably over 180 degrees.

In some embodiments, the thermally conductive means extends around the circumference of the cryogen chamber, preferably around the entire circumference thereof.

In these embodiments, the thermally conductive means may contact an interior surface of the cryogen chamber at one or more points, which may extend over a continuous or discontinuous area of the cryogen chamber, in a similar manner to the way in which the thermally conductive means may be arranged relative to the coil, as discussed above.

In some exemplary embodiments the thermally conductive means comprises one or more thermally conductive plugs which penetrate the cryogen chamber from the exterior thereof. In embodiments, the thermally conductive means extends between the plugs around the circumference of the interior of the cryogen chamber, preferably around substantially the entire circumference thereof. Preferably the thermally conductive means comprises a thermally conductive ring extending around the interior of the cryogen chamber, preferably around at least 80%, or 90%, or substantially 100% of the circumference of the cryogen chamber.

In use, the recondensation of cryogen creates a partial vacuum which drives the flow of cryogen vapour to the recondensing unit in a process known as cryopumping. The cryogen chamber may therefore comprise a mixture of liquid cryogen and vaporised cryogen at different stages in its cycle of vaporisation and recondensation as it travels from a region proximate the coil to the recondensing unit and back again.

The cryogen chamber may be provided in any manner which ensures that when a cryogen is located within the chamber in use, heat may be transmitted to the cryogen from the coil by the highly thermally conductive means even as the coil rotates. The cryogen chamber is a circumferentially extending chamber. The cryogen chamber extends circumferentially about the axis of the coil, i.e. it is coaxial with the coil axis.

The cryogen chamber is local to the superconducting coil. In other words, it is located in proximity thereto, and may be adjacent to the coil. For example, the chamber may be directly adjacent the coil, or separated therefrom by one or more intervening layers. The cryogen chamber is arranged such that cryogen located in the chamber in use does not directly contact the superconducting coil. In other words, the coil is not fully or partially immersed in liquid cryogen.

The cryogen chamber may be located in any position with respect to the coil provided that it may act to cool the coil in use. As the thermally conductive means provides a thermal path for heat transfer between the coil and the interior of the cryogen chamber, the cryogen chamber need not be coextensive with the coil. In some embodiments it may be axially spaced from the coil. The cryogen chamber may be located radially inwardly or outwardly relative to the coil. Thus, in embodiments the cryogen chamber is located axially and/or radially adjacent the coil. However, in preferred embodiments, the cryogen chamber at least partially surrounds the coil.

As the highly thermally conductive means transports heat to the interior of the cryogen chamber, the walls of the cryogen chamber may be of low thermal conductivity at cryogenic temperatures, e.g. less than 10 W/m/K. However, it is envisaged that the thermally conductive means might form a wall of the cryogen chamber in some embodiments.

It will be appreciated that as embodiments of the present invention need only contain a relatively small quantity of cryogen, the cryogen chamber may be relatively small in dimension, allowing a much more compact arrangement to be obtained than in conventional systems which immerse the coil fully or partially in a cryogen bath. The cryogen may be confined to a limited area around the coil axis defined by the position of the cryogen chamber. This provides the ability to make the superconducting coils, and other components of the system significantly smaller than conventional systems permit. Furthermore, as the quantities of cryogen used are relatively small, the system may be more economic to run, and the reduced consumption of cryogen may be advantageous in reducing demand on the already depleted supplies of cryogen, e.g. liquid helium, which may become more scarce in the future.

While the present invention allows the amount of cryogen present to be significantly reduced in comparison to conventional arrangements, it may be desirable to use volumes of cryogen which are larger than required to provide the ability for the system to continue to function if the cooler fails. The present invention may be applied to systems having cryogen chambers with a wide range of volumes, for example from 1 liter to 500 liter, or, in some embodiments from 2 liters to 100 liters.

In embodiments of the invention, the cryogen chamber has a circumferential extent. This enables cryogen in the chamber to continue to extract heat from the coil as the coil rotates about its axis in use. The cryogen chamber should extend circumferentially a sufficient distance around the axis of the coil to enable heat to be extracted when the coil is rotated through the angle of operation of the system in use. In embodiments, the cryogen chamber extends circumferentially around at least 75% of the axis of the coil, and preferably at least 90% of the axis of the coil. In preferred embodiments, the cryogen chamber extends substantially completely around the axis of the coil. The cryogen chamber may be annular. In preferred embodiments, the cryogen chamber surrounds the coil, and thus the cryogen chamber preferably extends a distance in the above ranges around the circumference of the coil. For example, the cryogen chamber may extend around at least 50%, more preferably at least 75%, or preferably the substantially the entire circumference of the coil.

In embodiments of the invention, the cryogen chamber is only partially filled with cryogen in use, allowing the cryogen to flow within the chamber as the coil rotates about its axis. The cryogen chamber should then have a circumferential extent sufficient to enable cryogen to flow in this manner as the coil rotates.

It will be appreciated that in embodiments in which more than one coil is present, one or more cryogen chambers may be provided associated with each superconducting coil of the system, or one cryogen chamber may be associated with more than one coil.

In accordance with the invention, once heat has been transferred from the coil to cryogen in the chamber, heat is transmitted the entire remaining distance to the recondensing unit by the cryogen. This is in contrast to some prior art systems in which solid thermal conductors transmit heat directly to the working fluid of the recondensing unit, and not to a liquid cryogen which is vaporised to act as a heat transport medium.

The cryogen chamber is connected to the recondensing unit in a manner which allows liquid or vaporised cryogen to travel between the cryogen chamber and recondensing unit in use. The cryogen chamber therefore comprises a port through which cryogen may flow to or from the recondensing unit. The port places the recondensing unit in fluid communication with the interior of the cryogen chamber. Preferably the cryogen chamber comprises only a single port. These embodiments may help to maximise the area of the cryogen chamber available for use as the coil rotates.

Preferably the port of the cryogen chamber is connected to the recondensing unit via at least one connecting pipe, i.e. a hollow pipe through which vaporised cryogen may flow. The pipe may be formed of a material which is of low thermal conductivity at cryogenic temperatures, and may have a thermal conductivity of less than 10 W/m/K. However, the thermal conductivity may be chosen with respect to the levels and rates of cooling required. Preferably the cryogen chamber comprises an outlet to the pipe. Preferably the connecting pipe is a rigid pipe.

It will be appreciated that where more than one coil and associated cryogen chamber is provided, each cryogen chamber may comprise a port for communicating with a recondensing unit. The recondensing unit may be the same or different. In some embodiments the ports associated with the cryogen chambers of each coil are connected to the recondensing unit via a common connecting pipe. However, in other arrangements, there may be one or more pipes associated with each cryogen chamber, and each pipe may be associated with one or more recondensing units, which may be the same or different. In systems comprising more than one pipe, the or each pipe may include any or all of the features described in relation to "the" pipe herein.

Preferably the pipe extends the entire distance between the cryogen chamber outlet and the recondensing unit, i.e. a cryogen contacting part thereof. It will be appreciated that where a plurality of coils are present, the recondensing unit may be associated with one or more coils, and there may be one or more recondensing units associated with each coil.

The connecting pipe may be of any suitable length. The length of the connecting pipe should be chosen so as to allow the recondensing unit to be located at a sufficient distance from the superconducting coil to reduce the risk of interference to the operation of the recondensing unit by the magnetic field associated with the coil, or conversely, the risk of interference to the operation of the particle accelerator by the recondensing unit. Typically, the larger the superconducting coil, the larger the stray magnetic field associated with the coil, and the further it may be necessary to locate the recondensing unit from the superconducting coil. In accordance with the invention, the recondensing unit may be located at distances as great as in the order of 1 m or more from the coil if necessary, allowing the cryocooler of the recondensing unit to be located out of a region subject to interference by the coil. In conventional arrangements using a thermal conductor to transport heat the entire distance from the coil to the recondensing unit, the size and mass of solid thermal conductor required to transport heat over a corresponding distance would be prohibitive. Preferably the recondensing unit is located at a distance of at least 60 cm, or more preferably at least 80 cm from the port communicating with the cryogen chamber. The recondensing unit may be located at any distance from the port within these ranges, and may be located at relatively great distances from the port if desired. In some embodiments, the recondensing unit may be located at a distance of no more than 140 cm, or no more than 120 cm from the port. The distance that the recondensing unit is located from the port may fall within any combination of the above ranges. The connecting pipe is therefore of a length in any of the above ranges.

Preferably the connecting pipe extends from the cryogen chamber to a relatively low magnetic field region. Thus, the recondensing unit end is in a lower magnetic field area than the cryogen chamber end.

The connecting pipe should be thermally insulated from the ambient temperature. This may be achieved using any suitable arrangement of vacuum spaces, intermediate shields and/or multi-layer insulation.

In preferred embodiments, the particle accelerator is rotatable in at least one direction, and preferably both directions, from a position in which the axis of the connecting pipe is vertical towards, and preferably to a position in which the axis of the connecting pipe is horizontal. In embodiments, the particle accelerator is rotatable to result in rotation of the coil about its axis through an angle of at least 45 degrees, and preferably between 45 and 90 degrees in either direction from a position in which the recondensing unit is located vertically above the axis of the coil. The cooling means will be operable to cool the coil as it rotates through these ranges of position.

Preferably the system is arranged to permit the recondensed cryogen to return to the cryogen chamber under the influence of gravity. In preferred embodiments, the system is arranged such that the particle accelerator may be rotated through a range of angles permitting the recondensed cryogen to return to the cryogen chamber under the influence of gravity, e.g. by dripping back down into the cryogen chamber.

It has been found that tapering of the pipe is helpful in promoting return of the recondensed cryogen to the cryogen chamber, facilitating operation of the system as the coil rotates about its axis through an angle of up to 180 degrees. The cryogen may more easily flow towards the cryogen chamber even when the axis of the connecting pipe is horizontal in these embodiments. Preferably the connecting pipe is tapered toward the recondensing unit. The connecting pipe may then provide a neck extending from the cryogen chamber.

The recondensing unit may be of any suitable construction. Preferably the recondensing unit comprises at least one cooling surface upon which cryogen may recondense in use. Preferably the recondensing unit comprises a cryocooler associated with the or each cooling surface. A cryocooler is a device well known in the art of low temperature superconductivity, and is a reciprocating heat engine which uses gas as a working fluid to transfer heat from one or more cold stages to room temperature. Preferably the recondensing unit thus comprises a working fluid. The cryocooler may be of any suitable construction which provides the required level of cooling of the cryogen for a given application. For example, larger coils e.g. of a larger magnet, will require greater levels of cooling power.

The present invention extends to a system in accordance with the invention in any of its aspects or embodiments including a cryogen. Preferably the cryogen is liquid helium.

In embodiments in which the cryogen chamber contains cryogen, to enable cooling of the coil as it rotates about the coil axis, the cryogen chamber is only partially filled with liquid cryogen. In preferred embodiments, the cryogen chamber is initially filled with liquid cryogen to a level of less than 50% of the height of the chamber. This is the level prior to use of the apparatus, and any vaporisation of the cryogen. It will be appreciated that, rotating of the coil and hence the cryogen chamber will result in the cryogen flowing around cryogen chamber to find its own level once again. In preferred embodiments, heat may still be transferred from regions of the coil or cryogen chamber other than those adjacent the cryogen by an appropriate configuration of the thermally conductive means to enable the entire, or a greater part, of the cryogen chamber to participate in cooling.

It will be appreciated that the system of the present invention includes a cryogen circuit, being the parts of the system through which cryogen may flow during its cycles of vaporisation and, preferably, recondensation. This circuit comprises the cryogen chamber, recondensing unit, and any connecting pipe or pipes.

In some embodiments of the invention, the cryogenic circuit is sealed, such that a fixed quantity of cryogen will be present throughout operation of the system, e.g. through cooldown, warmup, or quench. In some embodiments, the sealed circuit may incorporate an expansion vessel to accommodate the increased volume of the cryogenic working substance at higher temperatures e.g. room temperature. In other alternative embodiments, the sealed circuit may be of constant volume, and designed to withstand the additional pressure of the cryogenic substance at higher temperatures e.g. room temperature.

In some embodiments, the system comprises a cryogen reservoir for retaining gaseous cryogen for later recondensation at times when the evaporation rate of the cryogen exceeds the recondensation rate. This may occur, for example, when the system is started up, with the magnet being initially ramped to field.

As highly thermally conductive means is provided to facilitate transfer of heat between cryogen located in the cryogen chamber in use and the superconducting coil, and due to the use of a small cryogen chamber including a relatively low quantity of cryogen which is recondensed in use, the present invention provides a more compact arrangement than prior art arrangements including a conventional cryogen bath may provide, and by eliminating the need to immerse the coil in a bath of cryogen, greater freedom in the design of the system is provided. For example, the cryogen chamber may be located at a short distance from the coil to facilitate manufacture, or improve coil support and stress management for a given configuration of coil, and materials may be selected for the coil, and other surrounding parts, which need not necessarily be suitable for immersion in liquid helium.

In preferred embodiments the particle accelerator further comprises external coil support means for supporting the coil. The external coil support means is located radially outwardly of the coil. In preferred embodiments in which the cryogen chamber at least partially circumferentially surrounds the coil, the external coil support means is preferably located between the coil and the cryogen chamber. Due to the presence of the thermally conductive means, it is possible to locate a poor, or non thermally conductive layer between the cryogen chamber and superconducting coil without compromising the ability of the cryogen to cool the coil in use, as heat may still be transmitted to the cryogen via the thermally conductive means. In these embodiments of the invention, it has been found that the superconducting coil may operate in more extreme conditions than a coil wound conventionally on an internal former and cooled by a cryogen located directly adjacent and outward of the coil e.g. a helium bath.

In embodiments comprising the coil support, it is not necessary for the coils themselves to be self supporting. It may be possible in some applications to eliminate the need for any internal support of the coil. The use of an external support may maximise space available within the coil, and reduce attenuation of the effects of the coil in the region to the interior thereof, allowing reductions in the size of the coil. For example, a similar magnetic field may be obtained using a smaller diameter coil than in arrangements which rely upon the use of an internal support, allowing the apparatus to be made more compact.

The use of the coil support is particularly advantageous in that it allows further reductions in the size and weight of the superconducting coil to be achieved, providing a more lightweight and compact particle accelerator more suited to mounting to a support. The external coil support helps to resist the magnetic forces on the coil, which seek to expand it.

The external coil support at least partially circumferentially surrounds the coil or coils, and preferably substantially completely surrounds the coil or coils. In some embodiments the external support means is in the form of a collar. The coil support may share a common axis with the coil and particle accelerator (and cryogen chamber). In some embodiments the interior of the external coil support means comprises means for locating the or each coil. The means may be in the form of a recess. In embodiments comprising a pair of coils, the coils may be located at the axial ends of the support, and the coil support may extend axially between the coils along the common axis of the coils.

In embodiments including external coil support means, the support means may be or comprise any suitable material or materials to provide a required level of support for the coil, having regard to e.g. the size and configuration of the coil, and whether any additional support is present. Typically the external coil support means comprises or is formed of a different material to the highly thermally conductive means. In embodiments the external coil support means has a low thermal conductivity at cryogenic temperatures, for example in the range of less than 10 W/m/K. In embodiments the external coil support means has a lower thermal conductivity than the highly thermally conductive means at cryogenic temperatures. In some embodiments the support is a stainless steel support. The support is preferably selected to be non magnetic, i.e. a non magnetic grade of stainless steel.

In preferred embodiments in which the cryogen chamber surrounds the coil support means, the cryogen chamber extends over only a portion of the outer surface of the support means in the axial direction i.e. there are areas of the support means which are not adjacent the cryogen chamber in use.

In some embodiments, the cryogen chamber is defined at least in part by the external coil support. In preferred embodiments the support defines at least a (radially) inner wall of the cryogen chamber. In embodiments, the external surface of the support means comprises a circumferentially extending chamber therein which defines a part of the cryogen chamber. The cavity may be in the form of a channel defined in an outer surface of the support. It will be appreciated that in these embodiments, the channel will be closed to provide the cryogen chamber. In preferred embodiments, a cover plate is bonded to the exterior of the external coil support means to close the channel and provide the cryogen chamber. In these embodiments, a port should be provided in the plate at a given angular position for connection to a connecting pipe associated with the recondensing unit of the system. In preferred embodiments, the external coil support means and the plate are formed of the same material.

In embodiments comprising an external coil support means extending between the cryogen chamber and the coil, the highly thermally conducting means may extend around an axial end of the coil to be in thermal contact with the interior of the cryogen chamber. In embodiments in which the coil support defines the cryogen chamber with a cover plate, the highly thermally conductive means preferably penetrates the cover plate to be in thermal contact with the interior of the cryogen chamber. In embodiments the highly thermally conductive means comprises a plurality of plugs arranged around the circumference of the cover plate and penetrating the cover plate. Preferably the inner surface of the cover plate comprises highly thermally conductive means for distributing heat around the interior of the cryogen chamber. Preferably a ring of highly thermally conductive material is bonded to the inner surface of the cover plate. In embodiments in which the highly thermally conductive means comprises plugs penetrating the cover plate, the plugs are preferably in thermal contact with the thermally conductive material.

In accordance with the invention in any of its aspects and embodiments, the particle accelerator may be of any suitable construction capable of accelerating charged particles to provide an output beam of an appropriate strength for a desired application in use. For charged particle therapy applications, the particle accelerator should be arranged to produce a charged particle beam having an energy level sufficient to reach an intended target in a patient in charged particle therapy applications.

The general structure of such particle accelerators is well known, and any type comprising a superconducting coil, suitable for mounting to a support and which may be rotated may be used. In preferred embodiments, the particle accelerator is a cyclotron. The cyclotron may be, for example, a synchrocyclotron or an isochronous cyclotron.

In some embodiments, the particle accelerator comprises a vacuum chamber into which charged particles to be accelerated are introduced. In embodiments the system comprises a source for supplying charged particles to the vacuum chamber e.g. to a region in the center thereof in use. The vacuum chamber is located between the poles of the superconducting magnet coil. The vacuum chamber may be disc shaped. In embodiments, the particle accelerator comprises a pair of spaced electrodes or "does" defining a gap in the vacuum chamber for accelerating the charged particles. The electrodes may be arranged so as to be perpendicular to the magnetic field defined between the poles of the magnet. The particle accelerator comprises means for applying an alternating electric field to accelerate the charged particles, e.g. by providing an RF field across the electrodes. The particles are constrained by the electric field and the magnetic field to circulate in a spiral path as they are accelerated. This may be achieved by alternating the direction of the electric field. The particle accelerator is arranged such that accelerated particles are output from the particle accelerator output in the form of a beam. This may be achieved using any suitable beam extraction arrangement e.g. a collimator.

In preferred embodiments the particle accelerator comprises an outer yoke, and the superconducting coil assembly, including the external coil support, in embodiments in which external support means is provided for supporting the coil, is disposed within the yoke. The yoke preferably surrounds the superconducting coil. The other parts of the accelerator, e.g. electrodes, vacuum chamber etc. will accordingly also be located within the yoke in these embodiments. The yoke may provide the outer housing of the accelerator. Preferably the yoke is a ferromagnetic yoke of iron or steel. The yoke may comprise first and second sections which are fitted together around the coil assembly. In embodiments, the yoke is a pill box shaped yoke. The yoke may act to contain, concentrate and profile the magnetic field. The yoke may provide a path for return magnetic field flux and may magnetically shield the volume between the magnetic pole faces to prevent external magnetic fields influencing the magnetic field in this region, and my reduce the influence of any stray magnetic field in the area.

In embodiments in which the particle accelerator comprises an outer yoke, the recondensing unit is preferably located outside the yoke. This may help to locate the recondensing unit in a lower magnetic field area, and reduce the likelihood of interference between the recondensing unit and operation of the particle accelerator. In these embodiments the connecting pipe of the recondensing unit extends from the cryogen chamber through the yoke to the recondensing unit.

The system may comprise any suitable arrangements of shields, vacuum vessels and/or insulating layers associated with the coil/particle accelerator as known in the art.

The particle accelerator may further comprise a outer magnetic shield. The magnetic shield may, for example be a layer of ferromagnetic material. A space may be defined radially inwardly of the shield. In embodiments comprising a yoke, the magnetic shield is disposed outwardly of the yoke and is separated therefrom by a space.

The present invention extends to a particle accelerator for use in a system in accordance with the invention in any of its aspects or embodiments, and to a particle accelerator having cooling means to permit cooling of the coil as the coil rotates. It is believed that such a particle accelerator is advantageous in its own right, and in accordance with a further aspect of the invention there is provided;

a particle accelerator system comprising:
a particle accelerator having at least one annular superconducting coil for generating a magnetic field in use;
and cooling means for cooling the coil in use;
wherein the cooling means comprises:
a cryogen chamber situated local to the at least one superconducting coil for containing cryogen in use;
thermally conductive means arranged to facilitate heat transfer from the at least one superconducting coil to the cryogen chamber to vaporize cryogen contained therein in use and thereby remove heat from the at least one superconducting coil, the thermally conductive means being highly thermally conductive at cryogenic temperatures;
and a cryogen recondensing unit in fluid communication with the cryogen chamber, whereby vaporized cryogen may flow from the cryogen chamber to the cryogen recondensing unit to be recondensed in use before returning to the cryogen chamber;
wherein the cooling means is operable to cool the at least one superconducting coil upon movement of the particle accelerator resulting in rotation of coil about its axis in use.

The particle accelerator in accordance with this further aspect of the invention may include any or all of the features described in relation to the particle accelerator of the system of the earlier aspects of the invention. The particle accelerator is a rotatable particle accelerator system. For example, the cooling system etc may include any of the previously described features.

The present invention extends to a method of providing a system for cooling a superconducting coil in accordance with the invention according to any of its aspects and embodiments, and a method of cooling a superconducting coil using a system in accordance with the invention according to any of its aspects and embodiments. The method of cooling the coil may comprise the steps of providing cryogen in the cryogen chamber, and operating the superconducting coil whereby heat from the superconducting coil is conducted by the highly thermally conductive means to the cryogen chamber to vaporize the cryogen therein and thereby remove heat from the at least one coil, the vaporised cryogen flowing to the cryogen recondensing unit to be recondensed before returning to the chamber.

The present invention extends to the use of a system in accordance with any of the aspects and embodiments of the invention.

The present invention further provides a method of using the system in accordance with any of the aspects and embodiments of the invention, comprising operating the particle accelerator to provide an output beam of charged particles, and moving the particle accelerator to move the output beam, preferably through an arc, with rotation of the coil about its axis, with the cooling means operating to cool the coil as it rotates about its axis. The particle accelerator may be moved in any manner as described above, e.g. by rotating the support to which it is mounted and/or by rotating the particle accelerator relative to the support. In embodiments the system is a system for delivering charged particle therapy, and the method comprises operating the particle accelerator to provide an output beam of charged particles, directing the output beam towards a target to be irradiated, and moving the particle accelerator such that the beam is incident upon the target from different directions.

The present invention in these further aspects may include any or all of the features described in respect of the other aspects of the invention.

It will be appreciated that the terms "vertical" and "horizontal" as used herein are not intended to require that the relevant element is precisely "vertical" or "horizontal", but is at least approximately "vertical" or "horizontal". These terms are defined as commonly understood, and with respect to the system as oriented for its usual intended operation.

Some preferred embodiments of the present invention will now be described by way of example only, and with reference to the accompanying drawings of which:

FIG. 4B is a schematic view showing the relative positions of the patient, particle accelerator and output beam as the particle accelerator and patient support counter-rotate in the embodiment of FIG. 4A;

FIG. 6 is a vertical cross sectional view through the particle accelerator along the longitudinal axis, and corresponding to the line 6-6 in FIG. 13 showing the superconducting coil assembly including the coil, coil support, and cooling means in more detail and with certain other components of the particle accelerator removed for clarity;

FIG. 9 is a perspective view of the coil support;

FIG. 10 is a perspective view of the coil support with the coils mounted thereto;

FIG. 11 is a perspective view of the assembly of FIG. 10 with the cover plate mounted to the coil support to close the cryogen chamber;

FIG. 12 is a perspective view of the assembly of FIG. 11 with the thermally conductive means in place;

FIG. 13 is a perspective view of the assembly of FIG. 12 with the recondensing unit and connecting pipe assembled thereto;

Figure 2:
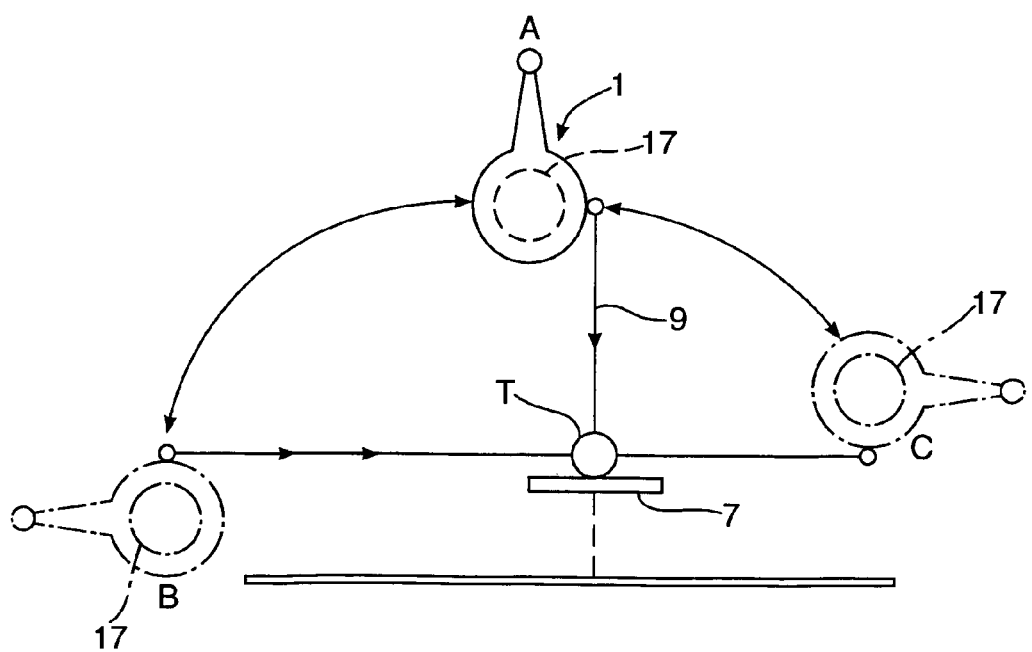
FIG. 2 is an end on view of the system of FIG. 1 illustrating the range of movement of the particle accelerator.
Figure 3:
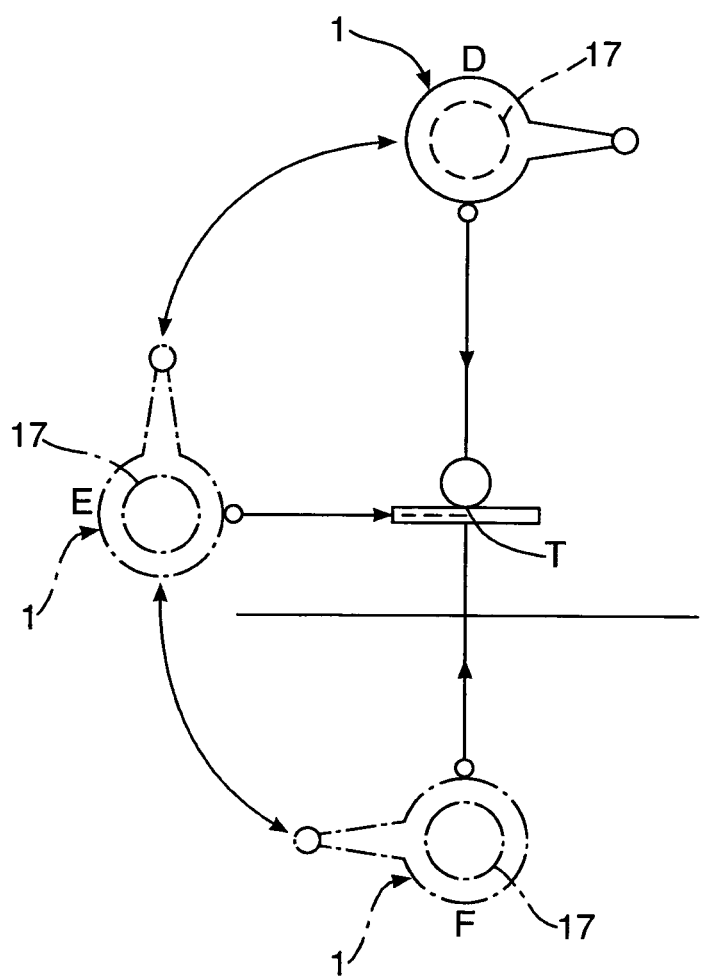
FIG. 3 is an end on view of another embodiment of a charged particle therapy system in accordance with the present invention, and similar to that of FIG. 1, but in which the particle accelerator is rotatable from a position vertically above a patient to vertically below.
Figure 14:
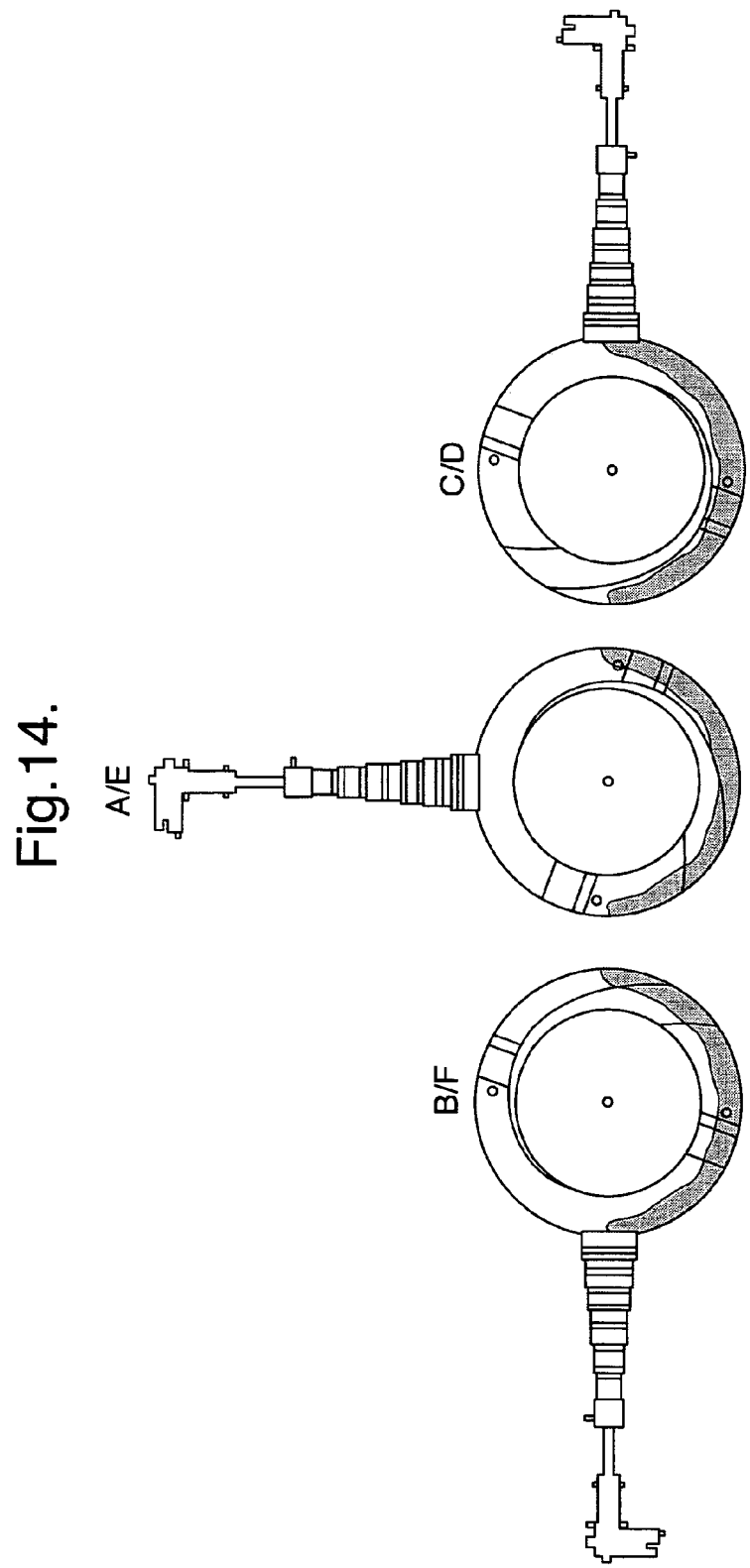

and FIG. 14 illustrates the position of the recondensing unit relative to the coil and support as the particle accelerator rotates between the positions shown in FIGS. 2 and 3.

Figure 1:
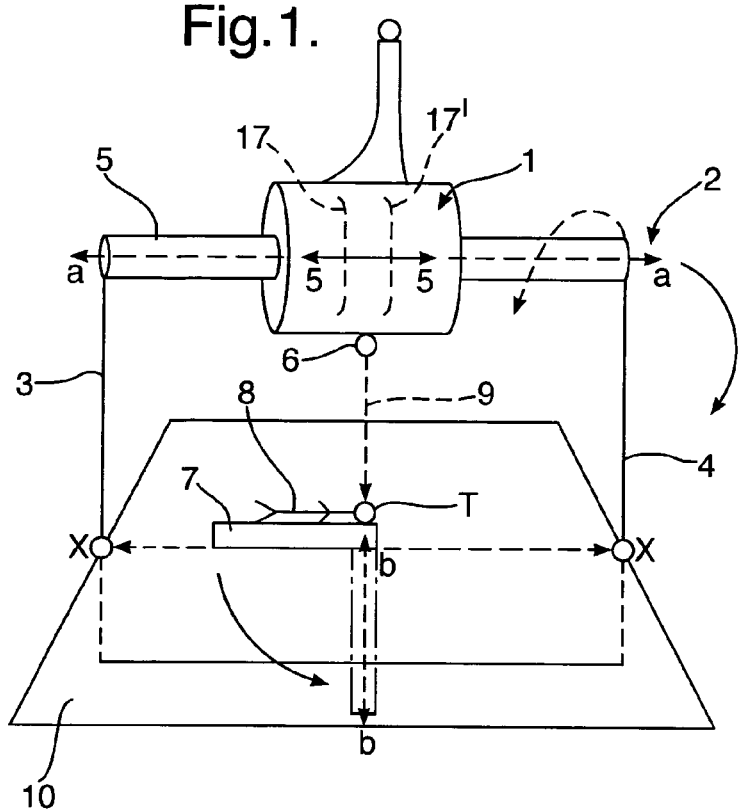
FIG. 1 is schematic view illustrating one embodiment of a charged particle therapy system in accordance with the present invention.

In accordance with the embodiment of FIG. 1, the particle accelerator 1 is mounted on a rotatable support in the form of gantry 2. The particle accelerator 1 includes superconducting coils 17, 17' as shown schematically in FIGS. 1 to 4 for generating a magnetic field when an electric current is passed therethrough in use. The gantry 2 is rotatable about a horizontal axis of rotation X-X from the position shown in FIG. 1 by up to 90 degrees in the clockwise and anticlockwise directions in the direction of the arrows. The gantry 2 includes a pair of legs 3,4 extending from the axis of rotation and an arm 5 extending therebetween to which the particle accelerator is mounted such that it rotates with the arm about the gantry axis of rotation. The axis a-a of the particle accelerator and its coils 17, 17' is parallel to the gantry axis of rotation X-X. The annular superconducting coils 17, 17' extend circumferentially about the coil axis. As the gantry 2 rotates, the particle accelerator 1 and its superconducting coils rotate about their axis as the particle accelerator 1 rotates with the gantry. A counterweight may be provided which counterrotates about the axis X-X as schematically illustrated. The particle accelerator may or may not also be rotatable about the axis of the gantry arm or another axis or axes.

The particle accelerator includes a nozzle 6 which is arranged to output a straight beam 9 of charged particles in use in a direction tangential to the particle accelerator. The beam is directed towards a target T in the region of a patient support 7 selected to result in irradiation of a target, such as a tumour, within a patient 8 lying supine on the support 7. When the particle accelerator 1 is in the position shown in FIG. 1, the beam is output in a vertical downward direction towards the target T. The target T is a point towards which the beam is directed that is chosen to result in irradiation of a particular position and depth within a patient when they lie on the support in use, e.g. to irradiate a tumour or other structure.

The range of rotational positions of the particle accelerator 1 in accordance with the embodiment of FIG. 1 is illustrated schematically in FIG. 2. The particle accelerator is rotatable from the position A shown in FIG. 1, where the gantry arm lies vertically above the gantry axis of rotation X-X through an angle of 90 degrees in either direction to the position B or C respectively, in which the gantry arm lies in a horizontal plane intersecting the horizontal gantry axis X-X. The particle accelerator 1 is therefore rotatable from a position A in which the beam 9 is incident on the target T on the patient support 7 from a position vertically above the target T to a position B or C in which the beam is incident upon the target T in a horizontal direction from either side of the patient support 7. As the gantry arm rotates, the particle accelerator rotates about its axis as a result of its mounting to the arm, causing the direction in which the output beam 9 is incident upon the target T to move through an arc. It will be appreciated that as the gantry arm 5 rotates, there is corresponding rotation of the coil 17 (and also coil 17') about their axes. The particle accelerator and coil have a common axis.

It will be appreciated that the system illustrated in the embodiment of FIGS. 1 and 2 may be used to irradiate a target T in the patient support from a range of directions spanning 180 degrees. When a patient lies on the support, this will allow irradiation of a structure within the patient from the corresponding range of directions, allowing irradiation from both sides of the patient. This is beneficial in that organs within the patient will tend to shift under gravity, and it is therefore important that the patient's position be fixed with respect to gravity in use.

In accordance with another embodiment, rather than being rotatable between the positions shown in FIGS. 1 and 2 such that the beam describes an arc defining the upper part of a circle as the gantry moves the particle accelerator, the particle accelerator is instead movable through 180 degrees from a position D as shown in FIG. 3, in which the beam is incident upon the target T from vertically above the patient, via a position E in which the beam moves horizontally, to a position F in which the beam is incident upon the target from vertically below the patient. In these embodiments the beam describes an arc defining the left part of a circle in use. These arrangements may be more space efficient than those of FIG. 2, and allow irradiation of a target in the patient from the posterior and anterior of the patient. The particle accelerator may instead move through the right half of a circle in a similar manner.

The cooling means is effective in cooling the coil as the particle accelerator is moved between positions A, B and C in FIG. 2, or positions D, E and F in FIG. 3. To this end, it will be seen that the orientation of the recondensing unit and pipe extending from the particle accelerator is different to enable the cryogen to return to the cryogen chamber under the action of gravity in each of these arrangements, as shown in more detail below.

In the embodiment shown in FIG. 1, 2 or 3, the patient support 7 may be arranged to rotate through up to 90 degrees in either direction about a vertical axis b-b as the particle accelerator is rotated to increase the solid angle from which the beam may be incident upon the target.

Figure 4A:
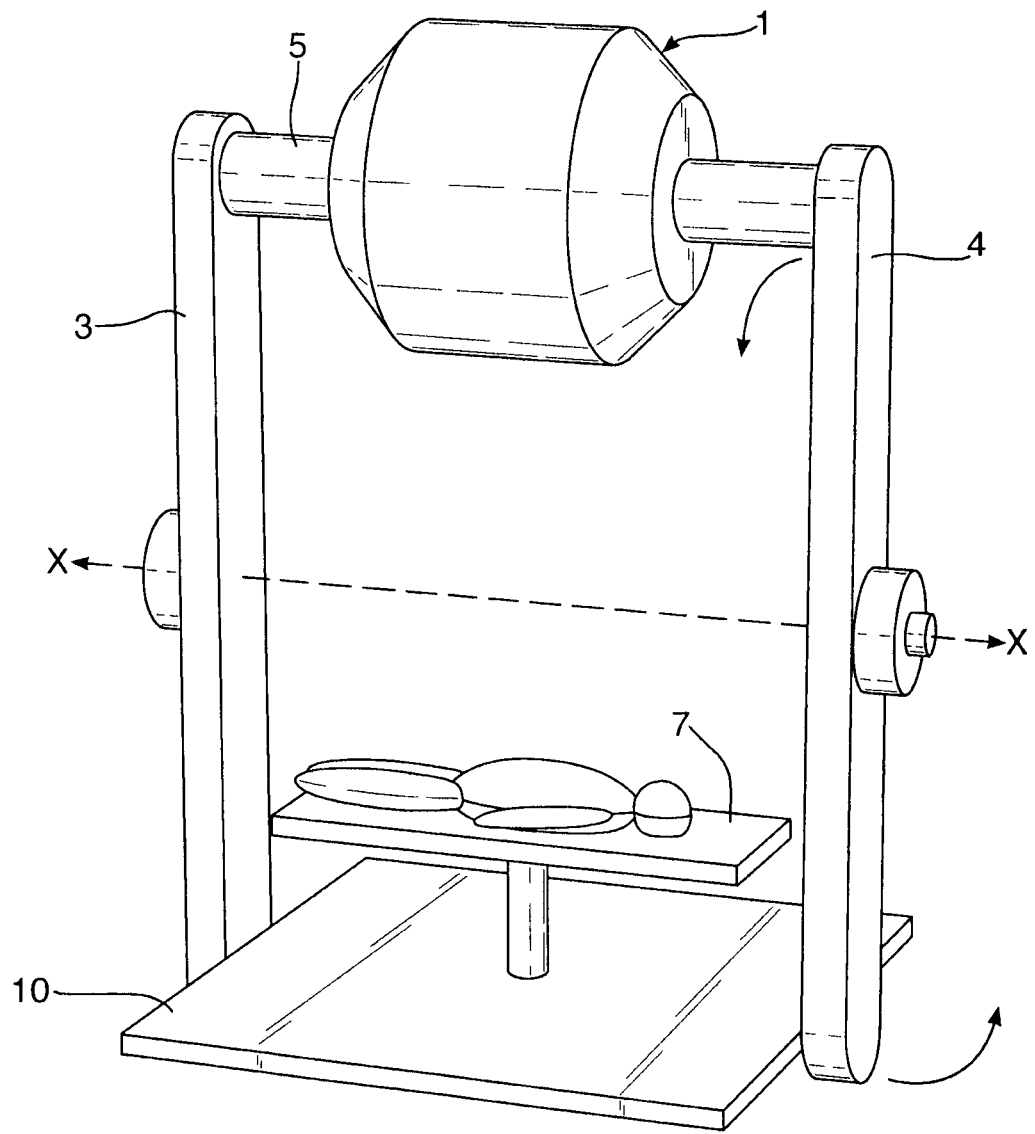
FIG. 4A is a schematic illustration of an embodiment of a charged particle therapy system in accordance with another embodiment of the invention in which the particle accelerator and patient support are arranged to counter-rotate about an intermediate axis.

FIG. 4A illustrates a further embodiment in which the patient support is arranged to counterrotate as the gantry rotates. In these embodiments the patient support may provide a counterweight to rotation of the gantry. For example, as the gantry and particle accelerator 1 rotate anticlockwise about the axis x-x, the floor 10 to which the patient support 7 is mounted rotates clockwise. Thus the patient support and particle accelerator rotate about the intermediate axis X-X. The patient support and particle accelerator may similarly rotate clockwise through up to 90 degrees when the particle accelerator rotates clockwise from the position shown in FIG. 4A.

FIG. 4B illustrates schematically the relative positions of the particle accelerator and patient support as they counterrotate.

It will be appreciated that rather than being mounted to a rotating gantry as shown in FIGS. 1-4B, the particle accelerator may alternatively be arranged to rotate relative to a support to cause rotation of the output beam and coil. The particle accelerator may be mounted on gimbals for this purpose. It is also envisaged that the particle accelerator could be rotatably mounted to a rotatable gantry in the embodiments of FIGS. 1-4B to provide a greater range of direction for the output beam, although it is not necessary for the particle accelerator to be able to move relative to the support, as rotation of the particle accelerator and hence coil about its axis will occur as described above, as a result of rotation of the support about the support axis of rotation. In any of the embodiments, the particle accelerator may be mounted to an arm, e.g. a robotic arm which is pivotally mounted to an axis of rotation for rotating the particle accelerator, rather than a gantry as shown.

In any of the arrangements, the particle accelerator may also be arranged to move so as to result in tilting of the coil axis, for example in the range of from 5 to 15 degrees. This may enable the coil axis to move out of a horizontal plane.

The features of the particle accelerator will now be described in more detail with respect to FIG. 5. For ease of illustration, FIG. 5 does not illustrate in detail all of the aspects of the system for cooling the superconducting coils e.g. thermally conductive means, cryogen chamber and pipe, and is intended to shown the main parts of the particle accelerator resulting in acceleration of the charged particles in use. The cooling system is described in more detail below.

Figure 5:
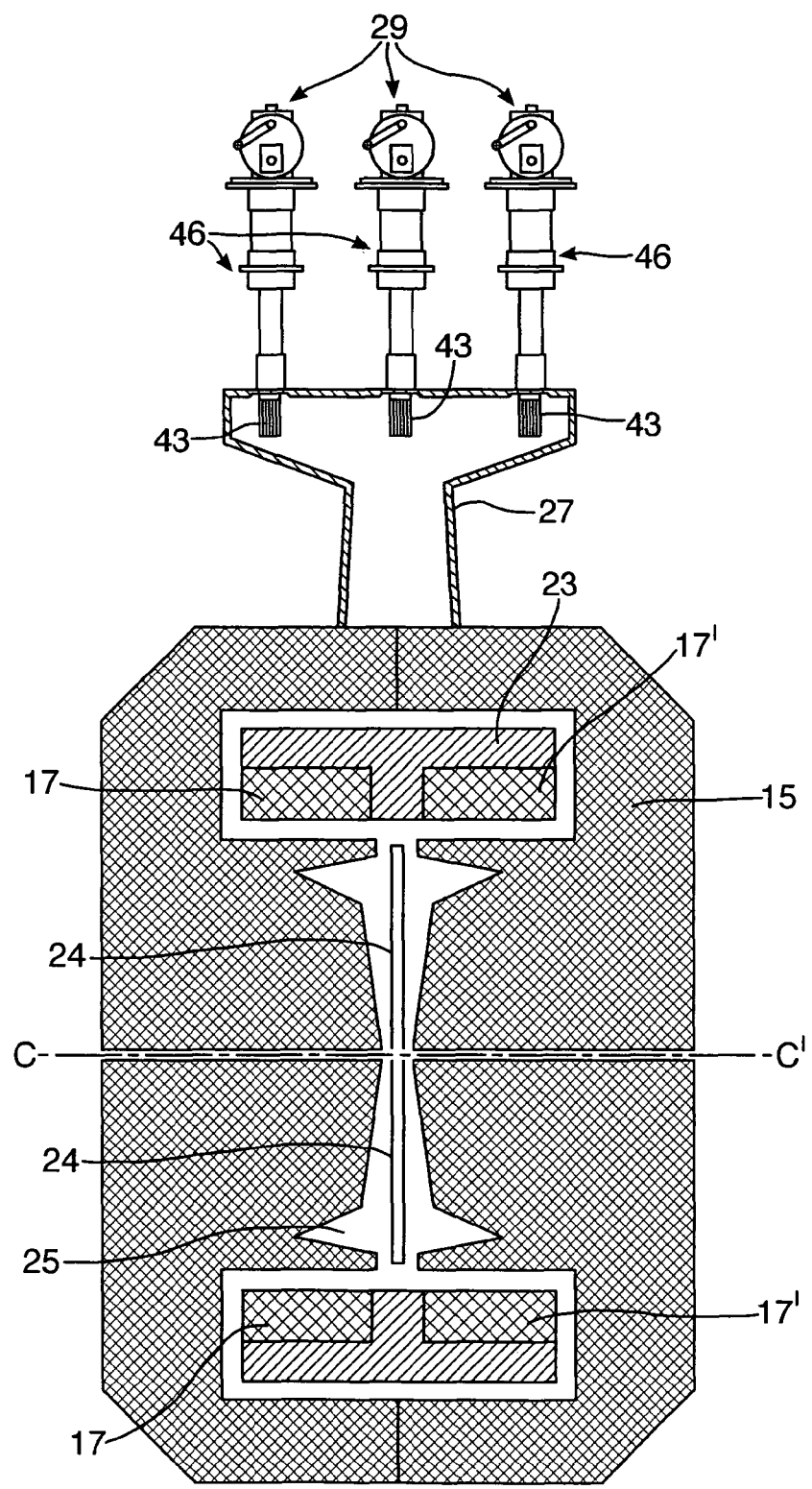
FIG. 5 is a vertical cross sectional view through the particle accelerator taken along the line 5-5 of FIG. 1.

Referring to FIG. 5, the particle accelerator 1 is a cyclotron arranged to accelerate charged particles useful in therapy. For example, these may be in the form of heavy ions, such as carbon, or protons. The particle accelerator 1 comprises an outer housing in the form of an iron yoke 15. The iron yoke 15 is of a pill box shape, and is formed from two halves. The iron yoke 15 is not essential. Within the yoke 15 is disposed a superconducting magnet comprising first and second annular superconducting coils 17, 17' mounted to recesses in the interior wall of a coil support 23 in the form of a non magnetic stainless steel collar. The coils 17, 17' are identical and are mounted on a common coil axis C-C, and are spaced from one another along the axis. The coil axis C-C corresponds to the particle accelerator axis. The superconducting coils 17, 17' are arranged to produce a magnetic field when an electric current is passed through them in use.

The operation of a cyclotron is well known. Briefly, the particle accelerator 1 includes a vacuum chamber 24 into the center of which particles to be accelerated are introduced from a particle source (not shown). The vacuum chamber 24 is located between the poles of the superconducting magnetic coils 17, 17'. The vacuum chamber is disc shaped. The particle accelerator 1 includes a pair of electrodes 27 or "dees" defining a gap in the vacuum chamber for accelerating the charged particles. In use, an alternating electric field is applied to the dees, which, together with the magnetic field generated by the superconducting magnet coils 17, 17' causes the particles to be accelerated in a spiral path. The electric field accelerates the particles between the dees in the magnetic field region, and is reversed at a cyclotron frequency to cause the particles to move in the spiral path. The particles are caused to form a beam and output via the nozzle 6 arranged tangentially to the particle accelerator.

A connecting pipe 27 extends through the iron yoke 15 to connect cryogen chambers associated with the coils with a recondensing unit 29 as described in more detail below.

In accordance with the invention, the particle accelerator comprises a cooling system for cooling the superconducting coils 17, 17', and which is effective even as the coils 17,17' rotate about their axis upon rotation of the gantry about the gantry axis. The cooling system will now be described with reference to FIGS. 6-8.

Figure 7:
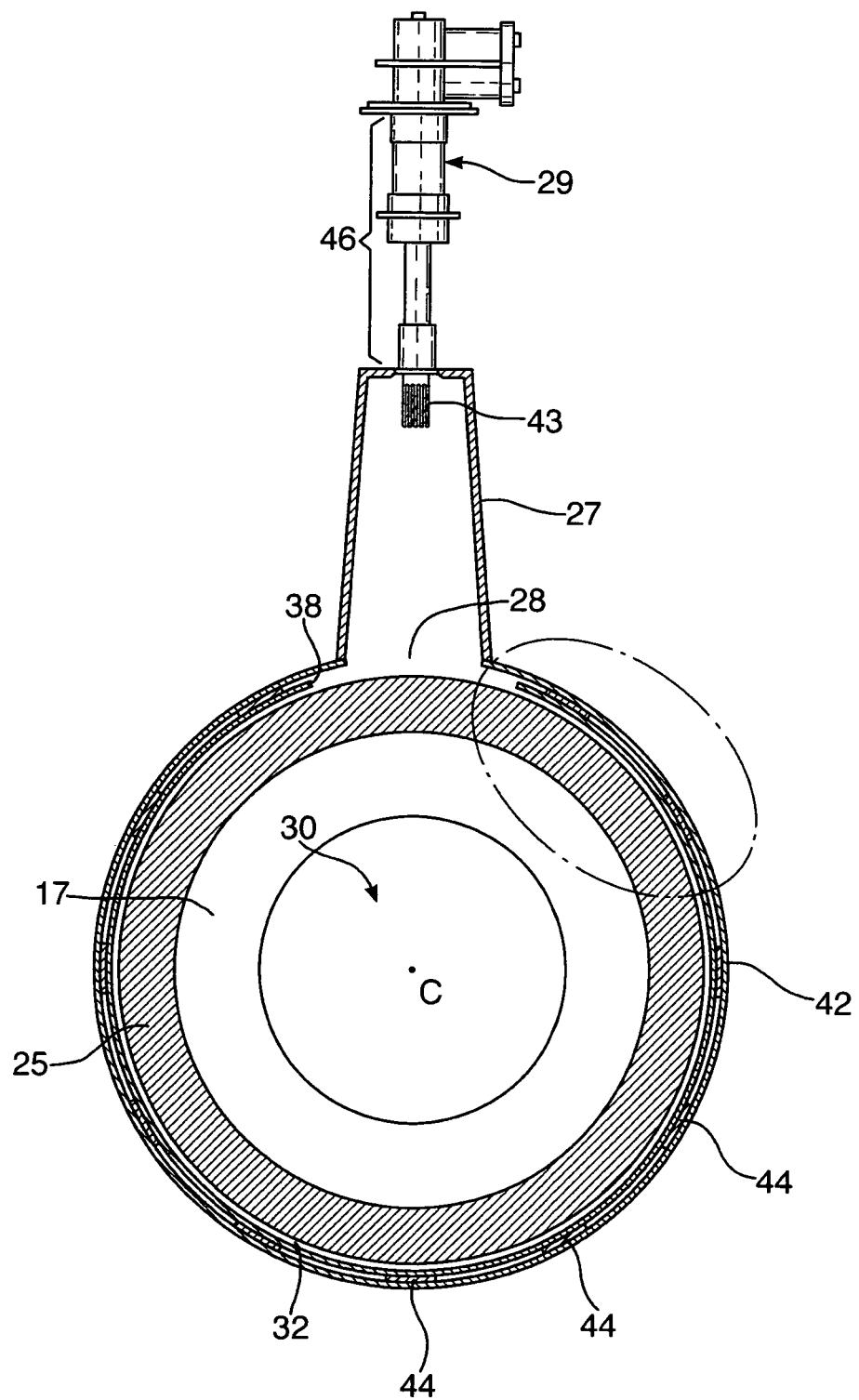
FIG. 7 is a vertical cross sectional view through the particle accelerator transverse to the coil axis along the line 7-7 of FIG. 13 showing the superconducting coil assembly including the coil, coil support, and cooling means in more detail and with certain other components of the particle accelerator removed for clarity.
Figure 8:
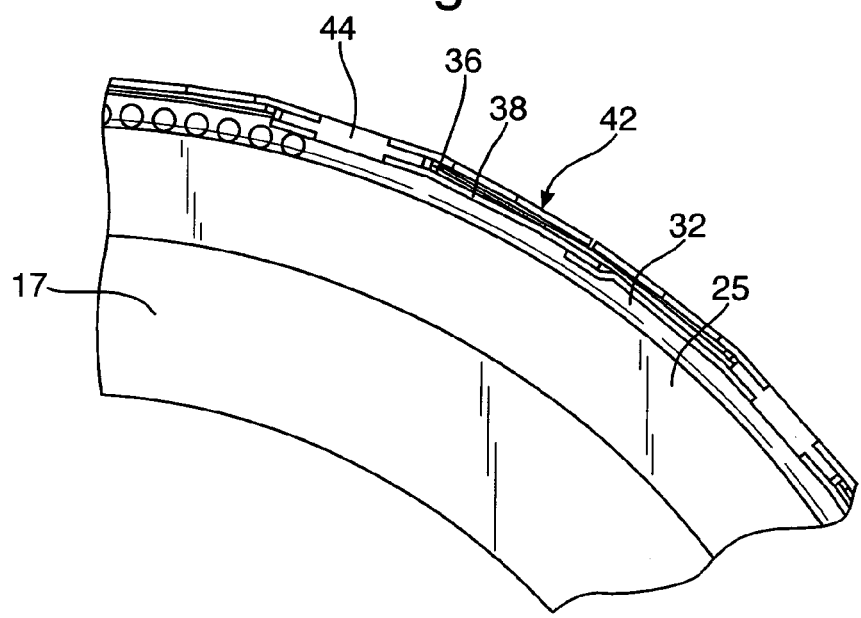
FIG. 8 is a detail taken in the circled region of FIG. 7.
Figure 13:
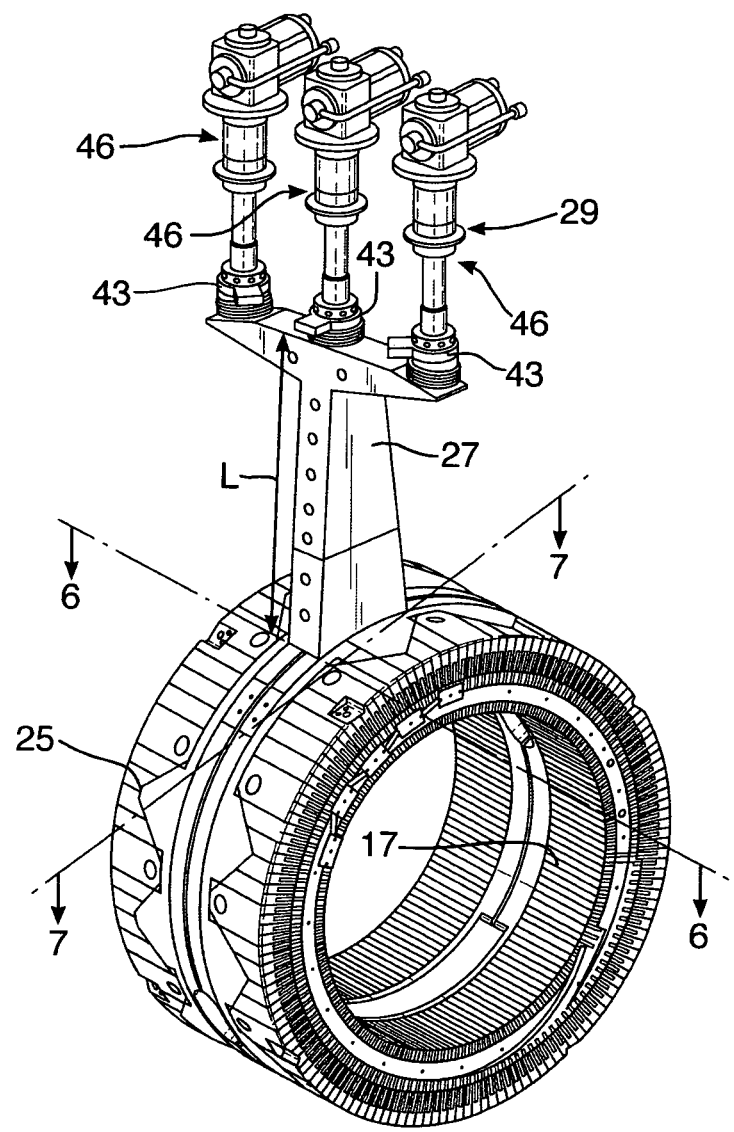

FIG. 6 is a vertical cross sectional view taken in the axial direction of the coils. This corresponds to the direction marked 6-6 in the perspective view of FIG. 13, showing the coil assembly. FIG. 7 is a vertical cross sectional view taken in the transverse direction of the coil 17. This corresponds to the line 7-7 of FIG. 13. FIG. 8 is a detail taken in the circled region of FIG. 7.

It will be appreciated that the construction of the system in the region of the second superconducting coil 17' is identical to that in the region of the coil 17, and thus, the present invention will be described in detail with respect to the first coil 17 and its associated cooling system. The corresponding parts of the system relating to the second superconducting coil 17' are denoted with the same reference numerals, but annotated with a prime ("'") sign. For simplicity, only the main features of the system in respect of the second superconducting coil 17' are labelled.

The coil 17 is a low temperature superconducting coil of niobium titanium or niobium tin, which materials behave as a superconductor only below a critical temperature (although it is envisaged that the system could be used in conjunction with other higher temperature superconducting coils, which also behave as superconductors only below a certain critical temperature). In the case of niobium titanium and niobium tin, the superconducting transition temperatures are 10.1K and 18.5K respectively. In order to provide good performance, and be able to carry large current densities in the presence of high magnetic fields, superconducting coils made of these materials must be cooled to well below the superconducting transition temperatures. The superconducting coil is not wound on any central mandrel, and is supported only by the external coil support 25 located radially outwardly of the coil. A cavity 30 is defined at the centre of the annular coil 17 within which the other parts of the particle accelerator shown in FIG. 5 are located in use.

The first superconducting coil 17 is mounted in a circumferentially extending recess 33 in the radially inner surface of the support means 25. The first superconducting coil 17 includes a radially outermost surface which contacts the inner surface of the external coil support 25. The support 25 is formed of a high strength non magnetic material which is of low thermal conductivity under cryogenic temperatures, such as stainless steel of a non magnetic grade. Stainless steel has a thermal conductivity of around 0.2 W/m/K at cryogenic temperatures. The support 25 is in the shape of a cylindrical collar. FIG. 7 shows more clearly how the support 25 circumferentially surrounds the entire perimeter of the coil 17, extending completely around the coil axis. The coil support 25 and coil have a common axis.

A cryogen chamber 32 is defined in part by the support 25. The cryogen chamber 32 is disposed radially outwardly of the support 25. A recessed channel 34 is provided in the outer surface of the support 25. The recessed channel 34 is spaced radially from the outer surface of the superconducting coil by the support 25.

A cover plate 36 which extends circumferentially around the support 25 is welded to the outer surface of the support 25 on either side of the channel 34 to close the channel and define the cryogen receiving chamber 32. The cover plate is shown in FIG. 6, but has been omitted from FIG. 7 for clarity.

FIG. 7 more clearly shows that the channel 34 extends circumferentially around the entire circumference of the coil support 25 in the region corresponding to the position of the superconducting coil 17 to provide the cryogen chamber 32. In use, as shown by the shaded part of the chamber 17 in FIGS. 6 and 7, the chamber is filled with a quantity of cryogen, such as liquid helium. The chamber extends all the way around the circumference of the coil and support, and hence the coil axis. In this way, a closed chamber 32 which extends circumferentially around the support 25 and superconducting coil 17 is provided, which is not in direct contact with the superconducting coil but instead is spaced therefrom by a portion of the low thermal conductivity support 25. At one angular position, the chamber 32 defines a port 26 in fluid communication with a recess 28 at the mouth of the connecting pipe 27 which leads to recondensing unit 29. The cryogen chamber 32' associated with the coil 17' similarly includes a port 26' at a corresponding angular position which is in fluid communication with the connecting pipe 27.

As the support 25 is of low thermal conductivity, or may not exhibit any thermal conductivity properties at all, in order to provide a thermal conduction path between the superconducting coil and the interior of the cryogen chamber 32, highly thermally conductive means 40 is provided. The highly thermally conductive means has a thermal conductivity at cryogenic temperatures in the order of at least 200 W/m/K at cryogenic temperatures. This is significantly greater than the thermal conductivity of materials conventionally used in the construction of structural parts of superconducting systems, such as, for example, stainless steel, aluminium alloy or glass reinforced polyester, which respectively have thermally conductivities at cryogenic temperatures of around 0.2 W/m/K, 2 W/m/K and 0.01 W/m/K. In the preferred embodiment the thermally conductive means comprises copper.

The highly thermally conductive means 40 comprises thermally conducting member 42 providing a continuous thermally conductive path linking the exposed surface of the coil to the cryogen chamber. The thermally conducting member 42 is bonded at one end to a radially inner surface of the superconducting coil 17 (see FIG. 6). The thermally conducting member 42 extends around the axial end of the coil 17 around the support 25 to the cryogen chamber 32. In the illustrated embodiment, the thermally conducting member 42 extends continuously around the entire circumference of the coil 17. The thermally conducting member 42 is segmented to avoid the risk of the thermally conducting member being able to sustain large eddy current and associated forces in the even of a magnet quench.

The thermally conducting member 42 terminates in a plurality of circumferentially spaced plugs 44 at the cryogen chamber end. As shown more clearly in FIG. 6, each plug 44 penetrates the cover plate 36 and is thermally connected to the other plugs by means of a ring of highly thermally conductive material 38 bonded to the plugs. The ring 38 comprises a plurality of sections of thermally conductive material bonded to, one another around the circumference of the device. The arrangement of the plugs 44, thermally conductive ring 38 and the cryogen chamber 32 is shown in more detail in FIG. 8, which is a detail in the circled region of FIG. 7.

The highly thermally conductive ring 38 is also bonded to the inner surface of the cover plate 36 which closes the cryogen chamber 32. In this manner, the highly thermally conductive ring 38 defines a part of the inner surface of the chamber 32. The highly thermally conductive member 42, the plugs 44 and the highly thermally conductive ring 38 are all formed of highly thermally conductive materials, such as copper. The plugs 44 may be electron beam welded to the highly thermally conductive ring 38. The components of the highly thermally conducting means are of higher thermal conductivity than the support 25.

As may be seen more clearly in FIG. 7, the thermally conductive means 40 extends circumferentially around the entire outer circumference of the cryogen chamber 32, being arranged radially outwardly thereof, with plugs 44 penetrating the cover plate defining the outer wall of the chamber at circumferentially spaced points. The thermally conductive ring 38 which is provided inside the cryogen chamber extends around the entire internal circumference of the interior of the cryogen chamber. In this manner, heat may be transmitted from any part of the coil to any part of the interior of the cryogen chamber, and the thermally conductive means 40 may distribute heat from a part of the cryogen chamber adjacent one part of the coil to a part adjacent another part of the coil. In practice, although cryogen is located in only the lower part of the cryogen chamber as shown in FIG. 7, heat may be transmitted from parts of the coil in the upper regions which are not adjacent a part of the cryogen chamber which is filled with cryogen to the lower part of the chamber in order to be absorbed by the cryogen to vaporize the cryogen by the thermally conductive means.

To facilitate understanding of the arrangement of the coil 17, the support 25, and the highly thermally conductive means 40 further, the assembly of the components to one another will be described with reference to FIGS. 9-13.

Figure 9:
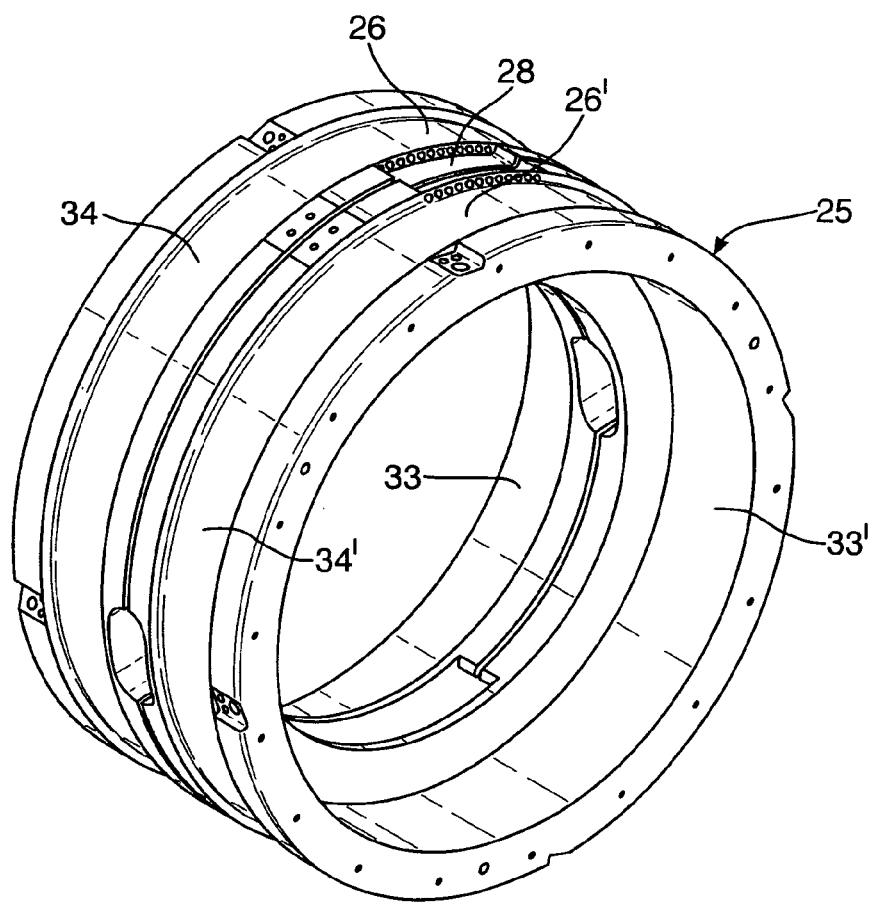
FIGS. 9-13 illustrate the steps in the assembly of the coil support, coils, and cooling means of the particle accelerator of the present invention.

FIG. 9 is a perspective view of the support 25 before the coils are mounted thereto, showing the internal recesses 33, 33' in the interior of the support 25 for receiving the coils 17,17'. The recessed channels 34, 34' in the outer surface of the support 25 which define the cryogen chambers 32, 32' with the cover plate 36, 36' may also be seen. The recesses 34 are provided with ports 26, 26' at one angular position which are in communication with a recess 28 over which the mouth of the connecting pipe 27 leading to the recondensing unit 29 is mounted in use to enable cryogen to move between each cryogen chamber 34, 34' and the recondensing unit 29 as described in more detail below.

Figure 10:
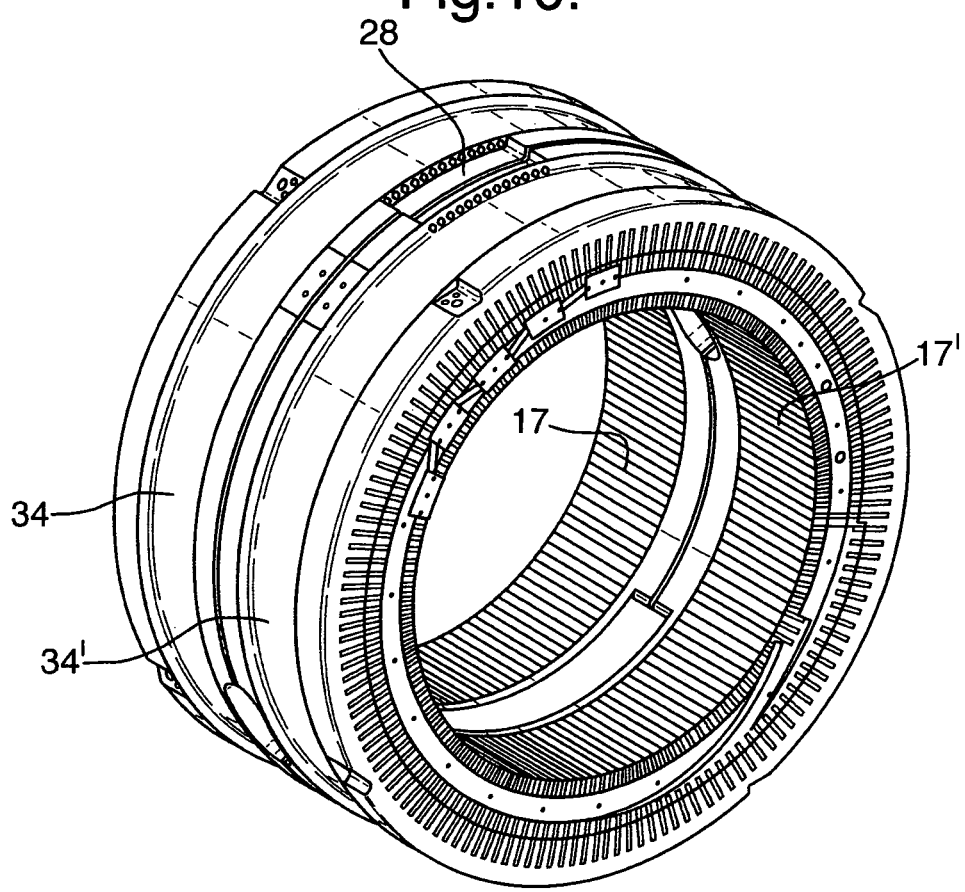

FIG. 10 illustrates the support shown in FIG. 9 once the coils 17, 17' have been mounted in the recesses 33, 33' respectively.

Figure 11:
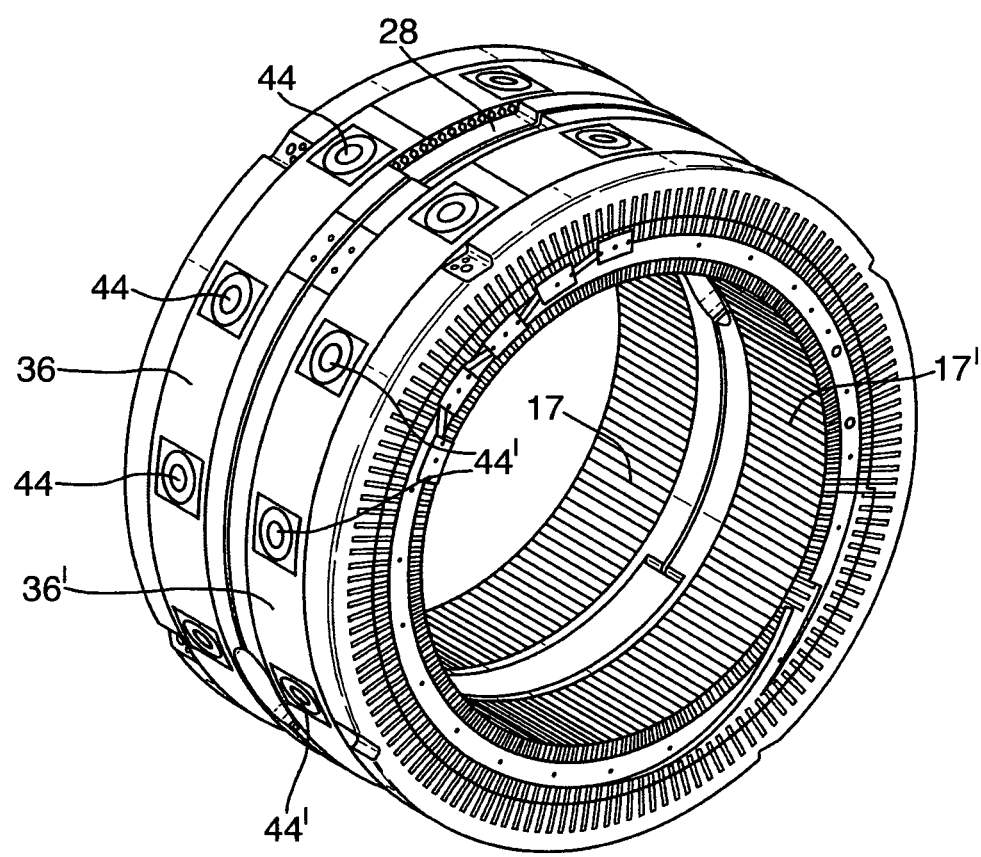

FIG. 11 illustrates the assembly of FIG. 10 after bonding of the circumferentially extending cover plates 36, 36' over the top of the recesses 34, 34' thereby defining the cryogen chambers 32, 32'. The thermally conductive plugs 44 may be seen penetrating the cover plate 36, 36' at a plurality of circumferential points. The thermally conductive plugs 44 are directly bonded to the thermally conductive ring 38 (not shown) to the interior of the cryogen chamber. It will be seen that the recess 28 which cooperates with the ports 26, 26' of each cryogen chamber 32, 32' remains exposed for receiving the mouth of the connecting pipe 27.

Figure 12:
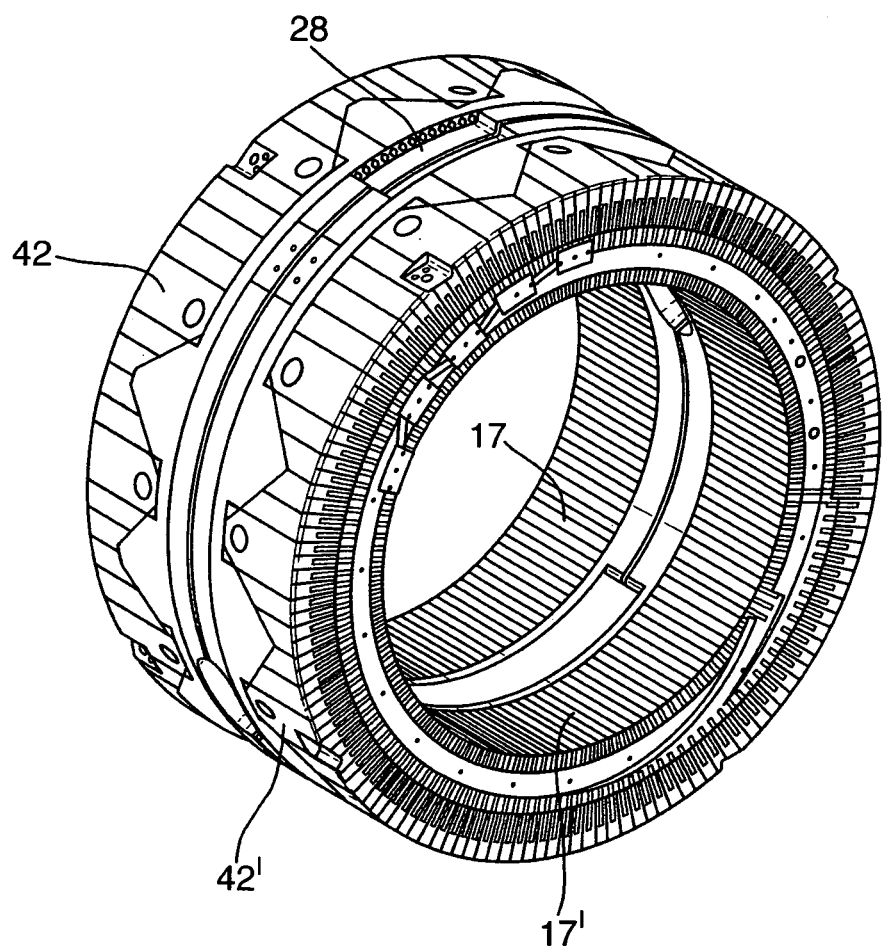

FIG. 12 illustrates the assembly of FIG. 11 once the highly thermally conductive members 42, 42' have been bonded at their respective ends to the plugs 44 and to the exposed surface of coils 17, 17' to provide a direct highly thermally conductive path between the coils and the interior of the cryogen chamber. The highly thermally conductive members 42, 42' extend around the axial ends of the coils.

As shown in FIG. 13, the connecting pipe 27 leading to the recondensing unit 29 is bonded over the recess 28 communicating with the ports 26, 26' of the cryogen chambers 32, 32'. In this way, the mouth of the pipe 27 is in fluid communication with the interior of the cryogen chambers 32, 32' to enable cryogen to flow between the recondensing unit and the cryogen chambers.

As may be seen most clearly in FIGS. 6, 7, and 13, the recondensing unit 29 comprises a plurality of cooling surfaces 43 connected to cryocoolers 46 which include a working fluid to enable vaporised cryogen which has passed from the cryogen chambers through the pipe 27 to the recondensing unit 29 to recondense before dropping back through the connecting pipe 27 into the cryogen chambers 32, 32' under the influence of gravity. The recondensing surfaces are kept at a temperature below the local cryogen boiling point, e.g. by being mechanically and thermally connected to the coldest stage of a cryocooler. The connecting pipe 27 is tapered toward the recondensing unit to promote movement of the cryogen back towards the cryogen chamber under the influence of gravity. As FIG. 5 shows, the connecting pipe 27 extends through the iron yoke of the particle accelerator to enable the recondensing unit 29 to be located in a low field region, reducing the risk of interference of the particle accelerator with its operation. The connecting pipe 27 has a length L of around 1 m. This corresponds to the distance that the recondensing surfaces 43 are located from the port to the cryogen chamber. This also reduces the risk of the recondensing units interfering with operation of the particle accelerator. The connecting pipe 27 is thermally insulated from ambient temperatures by a conventional arrangement of vacuum spaces, intermediate shields and multi-layer insulation.

The construction of the cooling system has been illustrated with respect to an arrangement in which the recondensing unit is vertical, i.e. corresponding to its position in FIG. 1, or position A of FIG. 2. However, the system is arranged such that it may still operate to cool the coil even if it is rotated through 90 degrees in either direction from this position, e.g. to position B or C as shown in FIG. 2, of from position E to position D or F in FIG. 3. The present invention therefore enables the particle accelerator to be rotated over 180 degrees with corresponding rotation of the coil about its axis without interfering with operation of the cooling system. It will be seen that in the arrangement of FIG. 3, the recondensing pipe is arranged to be vertical when the particle accelerator is located such that the beam is output horizontally, rather than when the beam moves vertically downward as in FIG. 2 to enable cryogen to return to the cryogen chamber under the action of gravity as the coil is rotated.

In use, cryogen is located in the cryogen chamber 32, 32' so as to partially fill the chamber to a level which is no more than 50% of the height of the chamber. This is illustrated in FIG. 7. As FIG. 14 illustrates, when the system is rotated through 90 degrees from the initial position A or E shown in FIG. 6, to position B/F or position C/D (referring to the corresponding positions in FIG. 2 or 3), the cryogen will flow within the chamber to find its own level. This is possible because the cryogen chamber extends a sufficient distance around the circumference of the coil to enable the cryogen to flow in this way, and because the cryogen does not completely fill the chamber. The position of the cryogen in the chamber is illustrated schematically by the shading in FIG. 14. As the coil is rotated about its axis through 180 degrees between positions B/F and C/D via position NE, the cryogen may continue to return to the cryogen chamber under the action of gravity once recondensed. The taper of the recondensing unit connecting pipe 27 facilitates return of cryogen to the cryogen chamber even when the axis of the pipe is horizontal as in positions B/F and C/D.

It will be appreciated that the highly thermally conductive means acts to distribute heat throughout the cryogen chamber 32 e.g. via the conducting ring 38 between parts of the cryogen chamber which are in contact with cryogen and parts which are not even as the system is rotated through 180 degrees to provide effective cooling.

Operation of the system to cool the coil 17, 17' will now be described. A liquid cryogen, such as liquid helium is located in the cryogen chamber 32, 32' as schematically illustrated in FIGS. 6 and 7, which show the cryogen as a shaded area. The liquid cryogen is initially filled to around 50% of the height of the cryogen chamber. In use, the superconductive coil 17 is operated as the particle accelerator 1 is used to provide an Output beam 9 for direction towards the target T. The particle accelerator 1 is initially located at position A, and the cryogen accordingly is located in the chamber relative to the recondensing unit as shown in FIG. 14, A. As the particle accelerator operates, heat is generated in the coils 17, 17'. Heat may also leak into the coils from a variety of sources when cold. The heat is transferred by thermal conduction from around the entire circumference of the coil via the highly thermally conductive means 40 to the interior of the cryogen chamber 17. The heat is conducted from around the circumference of the coil by the highly thermally conductive member 42, and transferred around the coil support 25 to the plugs 44 penetrating the cryogen chamber. The plugs 44 transfer the heat to the inner thermally conductive ring 38 which extends around the interior of the cryogen chamber. Heat delivered to one part of the cryogen chamber may therefore be distributed to other parts of the chamber by the conducting ring 38. In this way, even heat generated in upper regions of the coil, which are not radially adjacent to a part of the cryogen chamber 32 containing liquid cryogen, may be distributed to other parts of the cryogen chamber which do contain liquid cryogen by the thermally conductive means. As a result of the highly thermally conductive means 40, heat may still be transmitted to cryogen in a cryogen chamber despite the presence of the substantial low thermal conductive structural support 25 which is interposed between the coil and the cryogen chamber.

Heat reaching liquid cryogen in the chamber causes the cryogen to be vaporized. The vaporized cryogen moves upwardly in the direction of the arrows in 5 and 6 by diffusion towards the port 26 at the mouth 28 of the pipe 27 leading to the recondensing unit 29. The cryogen flows into contact with the recondensing surface and is cooled, thereby recondensing. The recondensed cryogen drops back down the pipe 27 and moves under the influence of gravity back into the cryogen chamber 32. The coil 17' is cooled in the same manner.

The process is the same as the gantry rotates to rotate the particle accelerator and its coil to position B or C shown in FIG. 2 to deliver the beam of particles to the target T from a different direction. The cryogen flows to a different position as shown in FIG. 14, but operation of the cooling system is unchanged. Operation is similar if the particle accelerator is moved between positions D, E and F as shown in FIG. 3.

In this manner, heat is removed from the superconducting coil by the vaporization and recondensation of the cryogen even when the coil rotates in use. It will be appreciated that heat is transferred away from the coil by two mechanisms. The heat travels from the coil to the cryogen in the cryogen chamber over the relatively short distance therebetween by a process of conduction via the thermally conductive means. The mechanism used to transfer heat from the cryogen chamber to the recondensing unit is one of diffusion with the cryogen itself acting as the thermal transfer medium. The recondensing unit may be located at any desired distance from the coil by using appropriate pipework. In this manner, the recondensing unit may be located such that it is out of the region which may be subject to interference due to any magnetic field produced by the superconducting coil, or other parts of the particle accelerator in use. The use of the cryogen as a heat transfer medium to transfer heat from the cryogen chamber to the recondensing unit over this relatively longer part of the heat transport path between the coil and recondensing unit may avoid the problem of significant temperature gradients arising, as may be experienced if solid conductors are used. Furthermore, the use of vaporised helium as the heat transfer medium may result in a significantly less bulky system, and make transport of heat over greater distances than would be realistic in practice using a thermal conductor possible. By way of example, to conduct 2 W of heat over a distance of 1 m, where there, is a temperature difference of 0.5K over the path length would by a rough illustrative calculation, require a solid copper thermal link with a conductivity of 600 W/m/K, having a diameter of around 100 mm and a mass in the order of 60 Kg. The mass of the conductor required is proportional to the square of the distance involved. It will be appreciated that the cryogen chamber is local to the superconducting coil in embodiments of the invention, and the thermal conduction is only required to take place over the short range. It has been found that the use of liquid cryogen as a heat transfer medium may also provide better vibration isolation between the recondensing unit and the superconducting coil.

As the superconducting coil does not need to be immersed in a bath or cryogen as in conventional arrangements, the support may be located to the exterior of the coil as shown in the illustrated embodiment. For example, the coil may be reinforced with a stiff collar on its outer surface if desired. This may allow the coil to operate in more extreme conditions than a coil wound conventionally on a mandrel or other internal support, and cooled by a helium bath located around its exterior surface.

As the coils are not supported by an internal former or surrounded by a helium bath, they may be made more compact, increasing their efficiency, and reducing the amount of superconductor required to generate a desired magnetic field. This enables reductions in the size and weight of the particle accelerator to be achieved, increasing the ease with which it may be mounted to a support for rotation, and providing a system which may be installed in a smaller space and at lower cost. This makes the system suitable for use in providing therapy in smaller and more widespread locations, such as district hospitals.

Furthermore, in contrast to conventional immersion type arrangements, a relatively small quantity of cryogen is required to be located in the cryogen chamber, and the cryogen chamber itself may be reduced in size to provide a more space efficient arrangement. This is because heat may be transported from all regions of the coil using thermally conductive elements to the cryogen chamber rapidly, and without significant losses, and heat may be distributed within the cryogen chamber to ensure that the amount delivered to that cryogen which is provided is maximized.

The cryogen circuit i.e. the cryogen chamber, pipe and recondensing unit, may be sealed, so that throughout the operating cycle, including cooldown, warmup and any quench which may occur, the circuit contains a fixed quantity of cryogenic substance. The sealed circuit may incorporate an expansion vessel to accommodate an increased volume of cryogen at room temperature. In other embodiments, the sealed circuit may be of constant volume, and may be designed to withstand the additional pressure of cryogen when warmed to room temperature.

As the amount of cryogen located in the system is relatively small, in the event that any quench does occur i.e. that the coil changes from a superconductive to a resistive state, converting its magnetic energy to heat, and causing vaporization to most or all of the cryogen, the amount of vapour released may be reduced, to the extent that it may be safely released to the environment, or collected for reuse. As cryogens, such as liquid helium, are likely to become relatively scarce resources, the ability to operate a system using a smaller quantity of helium and which allows the helium to be recycled, is advantageous.

The system may include a reservoir for containing vaporised cryogen to be recondensed when levels of evaporation of cryogen exceed levels of recondensation e.g. during initial ramp up of the superconducting magnet.

It has been found that the present invention may address certain conflicting requirement which may arise when designing a cooling system for a rotatable particle accelerator. The invention may allow reliable cooling of the superconducting coils to a low and stable temperature even as it is rotated. This allows lower temperature superconducting materials to be used in the coils, which generate relatively higher magnetic fields per unit mass, making it possible to decrease the overall size of the particle accelerator facilitating mounting, to the support e.g. gantry. The lower the temperature of operation of the coils, the smaller the quantity of wire which need be used in the coils, and the better the performance of the coils. The system does this without relying on immersion of the coils in cryogen, which undesirably increase the bulk of the system, and may eliminate any space/weight savings otherwise achieved by using superconducting coils. This is also achieved without relying solely on conduction cooling, avoiding the practical limits which arise as to the distance that the cryocoolers or other recondensing apparatus may be located from the particle accelerator and coils. In this way, the recondensing unit may be located relatively far from the coil, in a low field region, and where interference between the coil/particle accelerator and recondensing unit may be reduced.

By avoiding the need to have direct contact between cryogen and the coils, the present invention allows the coils to be supported externally. This enables further reductions in the size of the coils to be achieved, as they need not be self supporting. The present invention provides greater flexibility in the design of the coil support. In embodiments of the invention, the coils may support relatively high fields if they are supported externally, without significantly degrading performance. External supporting is advantageous in resisting the magnetic forces seeking to expand the coil in use. For example superconducting wire may incorporate copper to enhance the wire's stability against quenching. However, copper is comparatively weak, and high magnetic fields may result in unacceptably high levels of stress being generated in the windings, which may cause strain sufficient to degrade superconducting performance. Thus, in many cases it is desirable to reinforce coils, particularly ones intended to produce higher fields as desirable in the context of a support mounted particle accelerator. By allowing size reductions in the coil and cooling system to be achieved, the present invention may provide a system which may incorporate some coil reinforcement and still be suitable for gantry/support mounting.

The invention claimed is:

1. A system comprising:
   a support; and
   a particle accelerator mounted to the support for producing an output beam of charged particles in use, the particle accelerator comprising at least one annular superconducting coil for generating a magnetic field in use;
   means for cooling the superconducting coil in use, the cooling means comprises:
   a cryogen chamber situated local to the at least one superconducting coil for containing cryogen in use, the cryogen does not directly contact the at least one superconducting coil,
   thermally conductive means arranged to facilitate heat transfer from the at least one superconducting coil to the cryogen chamber to vaporize cryogen contained therein in use and thereby remove heat from the at least one superconducting coil, the thermally conductive means being highly thermally conductive at cryogenic temperatures, and
   a cryogen recondensing unit in fluid communication with the cryogen chamber, wherein vaporized cryogen may flow from the cryogen chamber to the cryogen recondensing unit to be recondensed in use before returning to the cryogen chamber;
   wherein the system is arranged such that the particle accelerator is movable to change the direction of the output beam in use, wherein the particle accelerator is rotatable to permit movement of the output beam through an arc in use;

and wherein the cooling means is operable to cool the superconducting coil as the coil rotates about its axis upon said movement of the particle accelerator in use, wherein the cooling means including the cryogen chamber, recondensing unit and thermally conductive means is arranged to rotate with the coil as the coil rotates about its axis.

2. The system of claim 1, wherein:
the support is arranged to be rotatable about a support axis of rotation, and the particle accelerator is mounted to the support such that it will rotate with the support about the support axis of rotation in use.

3. The system of claim 1, wherein:
the support is a gantry.

4. The system of claim 1, wherein:
the system is a system for delivering charged particle therapy, and wherein the system further comprises a patient support, and the system is arranged such that the output beam may be incident upon a target in the region of the patient support from different directions as the particle accelerator is moved in use.

5. A particle accelerator system comprising:
a particle accelerator having at least one annular superconducting coil for generating a magnetic field in use; and
cooling means for cooling the coil in use, the cooling means comprises:
  a cryogen chamber situated local to the at least one superconducting coil for containing cryogen in use, the cryogen does not directly contact the at least one superconducting coil;
  thermally conductive means arranged to facilitate heat transfer from the at least one superconducting coil to the cryogen chamber to vaporize cryogen contained therein in use and thereby remove heat from the at least one superconducting coil, the thermally conductive means being highly thermally conductive at cryogenic temperatures, and
  a cryogen recondensing unit in fluid communication with a cryogen chamber, wherein vaporized cryogen may flow from the cryogen chamber to the cryogen recondensing unit to be recondensed in use before returning to the cryogen chamber;
wherein the particle accelerator is rotatable to permit movement of an output beam through an arc in use; and
wherein the cooling means is operable to cool the at least one superconducting coil upon movement of the particle accelerator resulting in rotation of the coil about its axis in use, wherein the cooling means including the cryogen chamber, recondensing unit and thermally conductive means is arranged to rotate with the coil as the coil rotates about its axis.

6. The system of claim 5, wherein:
the particle accelerator is mounted to a support, wherein the support is arranged to be rotatable about a support axis of rotation, and the particle accelerator is mounted to the support such that it will rotate with the support about the support axis of rotation in use.

7. The system in accordance with claim 1, wherein the highly thermally conductive means is arranged to provide a direct thermal conduction path between a surface of the superconducting coil and the interior of the cryogen chamber.

8. The system in accordance with claim 1, wherein:
the highly thermally conductive means is arranged such that it may conduct heat from a part of the cryogen chamber which does not contain cryogen in use to a part of the cryogen chamber which does contain cryogen in use as the coil rotates about its axis in use.

9. The system in accordance with claim 1, wherein:
the cryogen chamber has a circumferential extent about the axis of the at least one superconducting coil, and is located axially and/or radially adjacent to the at least one superconducting coil.

10. The system of claim 9, wherein:
the cryogen chamber at least partially circumferentially surrounds the at least one superconducting coil.

11. The system of claim 1, wherein:
the cryogen chamber extends circumferentially at least 50% around the axis of the at least one superconducting coil.

12. The system of claim 1, wherein:
the cryogen chamber extends circumferentially at least 70% around the axis of the at least one superconducting coil.

13. The system of claim 1, wherein:
the cryogen chamber extends substantially completely around the axis of the at least one superconducting coil.

14. The system of claim 1, wherein:
the system is arranged such that recondensed cryogen may return to the cryogen chamber under the influence of gravity.

15. The system according to claim 1, wherein:
the system further comprises external support means for supporting the coil, the support means at least partially circumferentially surrounding the coil.

16. The system in accordance with claim 1, further comprising:
cryogen in the cryogen chamber, and wherein the chamber contains liquid cryogen which fills the cryogen chamber to a level of less than 50% of the height of the chamber.

17. The system of claim 1, wherein:
the cooling means is operable to cool the coil as the coil rotates through an angle of at least 90 degrees upon movement of the particle accelerator.

18. The system of claim 1, wherein:
the cooling means is operable to cool the coil as the coil rotates through an angle of up to 180 degrees upon movement of the particle accelerator.

19. A system for delivering charged particle therapy in use, the system comprising:
a patient support,
a particle accelerator support;
a particle accelerator mounted to the particle accelerator support and being arranged to output a beam of charged particles towards a target in the region of the patient support in use, the particle accelerator comprising at least one annular superconducting coil for generating a magnetic field in use; and
means for cooling the superconducting coil in use, the means for cooling comprises:
  a cryogen chamber situated local to the at least one superconducting coil for containing cryogen in use, the cryogen does not directly contact the at least one superconducting coil,
  thermally conductive means arranged to facilitate heat transfer from the at least one superconducting coil to the cryogen chamber to vaporize cryogen contained therein in use and thereby remove heat from the at least one coil, the thermally conductive means being highly thermally conductive at cryogenic temperatures, and
  a cryogen recondensing unit in fluid communication with the cryogen chamber, wherein vaporized cryogen may flow from the cryogen chamber to the cryogen recondensing unit to be recondensed in use before returning to the cryogen chamber;

wherein the system is arranged such that the particle accelerator is movable to change the direction of the output beam in use;

wherein the particle accelerator is rotatable to permit movement of the output beam through an arc in use;

wherein the cooling means is operable to cool the superconducting coil as the coil rotates about its axis upon said movement of the particle accelerator in use, wherein the cooling means including the cryogen chamber, recondensing unit and thermally conductive means is arranged to rotate with the coil as the coil rotates about its axis.

20. The system of claim 19, wherein:

the particle accelerator support is arranged to be rotatable about a particle accelerator support axis of rotation, and the particle accelerator is mounted to the particle accelerator support such that it will rotate with the particle accelerator support about the particle accelerator support axis of rotation in use.

21. The system of claim 1 further comprising:

the cryogen recondensing unit is in fluid communication with the cryogen chamber via a connecting pipe.

22. The particle accelerator system of claim 5 further comprising:

the cryogen recondensing unit is in fluid communication with the cryogen chamber via a connecting pipe.

23. The system of claim 19 further comprising:

the cryogen recondensing unit is in fluid communication with the cryogen chamber via a connecting pipe.

24. The system of claim 1 further comprising:

the cryogen recondensing unit is in fluid communication with the cryogen chamber via a connecting pipe, the connecting pipe being tapered towards the cryogen recondensing unit.

25. The system according to claim 1, wherein:

the system further comprises external support means for supporting the coil, the support means at least partially circumferentially surrounding the coil, wherein the support means is located between the superconducting coil and the cryogen chamber.

* * * * *